United States Patent
Dobb et al.

(10) Patent No.: US 9,447,093 B2
(45) Date of Patent: Sep. 20, 2016

(54) 3,5-DIARYLAZAINDOLES AS DYRK1A PROTEIN INHIBITORS FOR THE TREATMENT OF COGNITIVE DEFICIENCIES ASSOCIATED WITH DOWN'S SYNDROME AND WITH ALZHEIMER'S DISEASE

(71) Applicants: Centre National De La Recherche Scientifique, Paris (FR); Universite de Reims Champagne-Ardenne, Reims (FR); Universite Paris Diderot Paris 7, Paris (FR)

(72) Inventors: Robert Dobb, Paris (FR); Kevin Cariou, Paris (FR); Stephanie Gourdain, Gif sur Yvette (FR); Jean Maurice Delabar, Kremlin Bicetre (FR); Nathalie Janel, Paris (FR); Fernando Rodrigues Lima, Saint Maurice (FR); Julien Dairou, Boulogne-Billancourt (FR); Clement Denhez, Reims (FR)

(73) Assignees: Centre National De La Recherche Scientifique (CNRS) (FR); Universite de Reims Champagne-Ardenne (FR); Universite Paris Diderot Paris 7 (FR)

( * ) Notice: Subject to any disclaimer, the term of this patent is extended or adjusted under 35 U.S.C. 154(b) by 0 days.

(21) Appl. No.: 14/653,570

(22) PCT Filed: Dec. 18, 2013

(86) PCT No.: PCT/EP2013/077224
§ 371 (c)(1),
(2) Date: Jun. 18, 2015

(87) PCT Pub. No.: WO2014/096093
PCT Pub. Date: Jun. 26, 2014

(65) Prior Publication Data
US 2015/0307492 A1 Oct. 29, 2015

(30) Foreign Application Priority Data

Dec. 18, 2012 (FR) ...................... 12 62275

(51) Int. Cl.
*C07D 401/02* (2006.01)
*C07D 401/10* (2006.01)
*C07D 471/04* (2006.01)

(52) U.S. Cl.
CPC .................. *C07D 471/04* (2013.01)

(58) Field of Classification Search
CPC .................. C07D 401/02; C07D 401/10
USPC ......................... 546/121; 514/300
See application file for complete search history.

(56) References Cited

FOREIGN PATENT DOCUMENTS

| WO | 2004/078756 A2 | 9/2004 |
| WO | 2005/095400 A1 | 10/2005 |
| WO | 2006/063167 A1 | 6/2006 |
| WO | 2007/106236 A2 | 9/2007 |
| WO | 2008/124849 A2 | 10/2008 |
| WO | 2011/149950 A2 | 12/2011 |

OTHER PUBLICATIONS

Gourdain et al., Journal of Medicinal Chemistry (2013), 56(23), 9569-9585.*
Debdab, Mansour et al. "Leucettines, a Class of Potent Inhibitors of cdc2-Like Kinases and Dual Specificity, Tyrosine Phosphorylation Regulated Kinases Derived from the Marine Sponge Leucettamine B: Modulation of Alternative Pre-RNA Splicing" J. Med. Chem. 2011, 54, 4172-4186.
Hong, Seunghee et al. "Design, Synthesis, and Evaluation of 3,5 Disubstituted 7-Azaindoles as Trk Inhibitors with Anticancer and Antiangiogenic Activities" J. Med. Chem. 2012, 55, 5337-5349.
Klumpp, Martin et al. "Readout Technologies for Highly Miniaturized Kinase Assays Applicable to High-Throughput Screening in a 1536-Well Format" Journal of Biomolecular Screening, 2006, 617-633.
Meijer, Laurent et al. "Meriolins (3-(Pyrimidin-4-yl)-7-azaindoles): Synthesis, Kinase Inhibitory Activity, Cellular Effects, and Structure of a CDK2/Cyclin A/Meriolin Complex" J. Med. Chem. 2008, 51, 737-751.
Neagoie, Cleopatra et al. "Synthesis of chromeno[3,4-b]indoles as Lamellarin D analogues : A novel DYRK1A inhibitor class" European Journal of Medicinal Chemistry, 2012, 49, 379-396.
Woods, Yvonne et al. "The kinase DYRK1A phosphorylates the transcription factor FKHR at Ser329 in vitro, a novel in vivo phosphorylation site" Biochem. J., 2001, 355, 597-607.
Woods, Yvonne et al. "The kinase DYRK phosphorylates protein-synthesis initiation factor eIF2Be at Ser539 and the microtubule-associated protein tau at Thr212 : potential role for DYRK as a glycogen synthase kinase 3-priming kinase" Biochem. J., 2001, 355, 609-615.

* cited by examiner

*Primary Examiner* — Niloofar Rahmani
(74) *Attorney, Agent, or Firm* — Banner & Witcoff, Ltd.

(57) ABSTRACT

The present invention discloses compositions of novel DYRK1A protein inhibitors based on a 3,5-diarylazaindole motif and their preparation and use as medications in the treatment of cognitive disorders associated with dysfunction of DYRK1A protein, with Down's syndrome and with Alzheimer's disease.

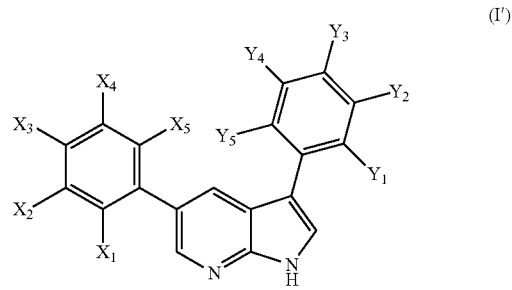

24 Claims, 1 Drawing Sheet

Figure 1A:
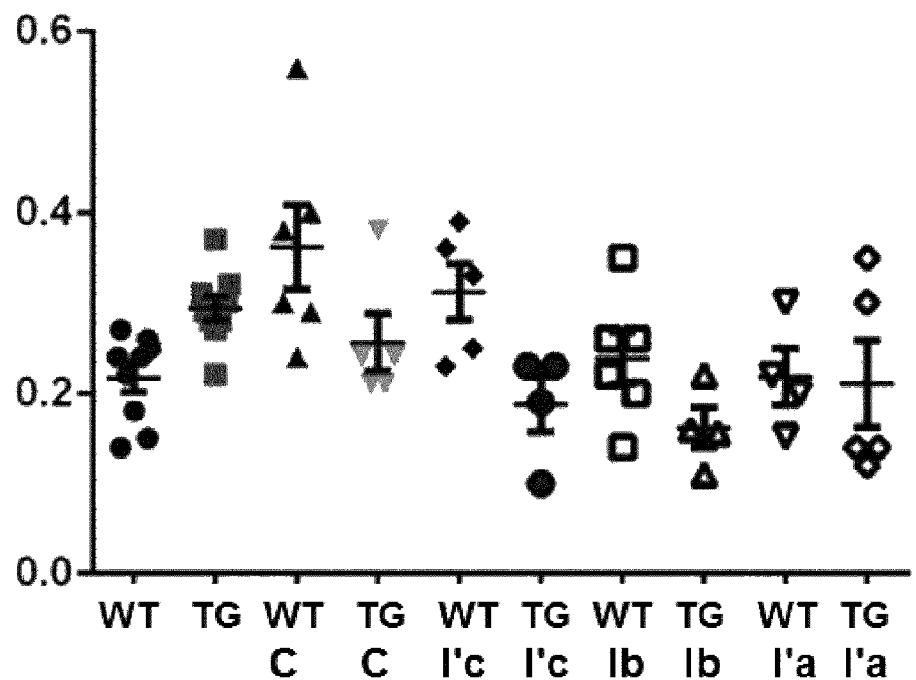

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: kinase substrate

<400> SEQUENCE: 1

Ile Ser Gly Arg Leu Ser Pro Ile Met Thr Glu Gln
1               5                   10

<210> SEQ ID NO 2
<211> LENGTH: 14
<212> TYPE: PRT
```

```
<213> ORGANISM: Artificial Sequence
<220> FEATURE:
<223> OTHER INFORMATION: kinase substrate

<400> SEQUENCE: 2

Lys Lys Ile Ser Gly Arg Leu Ser Pro Ile Met Thr Glu Gln
1               5                   10
```

3,5-DIARYLAZAINDOLES AS DYRK1A PROTEIN INHIBITORS FOR THE TREATMENT OF COGNITIVE DEFICIENCIES ASSOCIATED WITH DOWN'S SYNDROME AND WITH ALZHEIMER'S DISEASE

The present invention relates to novel DYRK1A protein inhibitors based on a 3,5-diarylazaindole motif and to the use of same as medications, particularly in the treatment of cognitive disorders associated with dysfunction of DYRK1A protein.

Dual specificity tyrosine-regulated kinase 1A (DYRK1A) protein is a serine/threonine kinase expressed in the fetal brain and in the adult brain. This protein is involved in the development of the human brain and maintenance of its normal functioning. Its role is essential to processes involved in learning, memorization and cognition. In humans, the gene encoding this protein is carried on chromosome 21.

Down's syndrome (trisomy 21) is a congenital genetic disease which is found in nearly 1 in 700 births in the United States and which represents nearly 40% of mild to severe cases of mental retardation in adults. In individuals suffering from full or partial trisomy 21 associated with the critical portion of chromosome 21 (Down syndrome critical region, or DSCR), the gene encoding the protein is triplicated and DYRK1A protein is then synthesized at a rate 1.5 times higher than the normal rate. It has been shown in murine models that this DYRK1A protein overexpression was involved in cerebral and cognitive changes associated with Down's syndrome.

Recent studies have shown, among other things, that DYRK1A protein was involved in phosphorylation of the microtubule-associated protein tau. Aberrant phosphorylation of this protein leads to intracellular aggregation of these proteins, one of the causes of the development of Alzheimer's disease.

Alzheimer's disease is a neurodegenerative disorder that affects about 24 million people worldwide. The symptoms of this disease are difficulty in remembering recent events and cognitive deficits which affect a variety of functions, such as motor function, language, memory, perception and cognition.

Compounds for inhibiting DYRK1A protein are thus of great interest with regard to treatment of cognitive disorders associated with Down's syndrome and to the prevention and/or treatment of changes in cognitive processes associated with Alzheimer's disease.

DYRK1A protein inhibitors have already been described in the prior art. One of the first DYRK1A protein inhibitors shown was harmine, a natural β-carboline. Synthetic analogs were then prepared, primarily based on aromatic nuclei, for example of type indol and aminoimidazole.

Debdab et al. (Journal of Medicinal Chemistry 2011, 54, 4172-4186) describes the use of a compound extracted from a marine sponge, leucettamine B, and of synthetic derivatives based on a 2-aminoimidazolin-4-one motif (leucettines). The most effective compound has an inhibitory activity ($IC_{50}$) on DYRK1A protein of about 40 nM.

Neagoie et al. (European Journal of Medicinal Chemistry, 2012, 49, 379-396) describes chromenones and the inhibitory capacity thereof on DYRK1A protein. The most effective compound has an $IC_{50}$ of about 70 nM and good selectivity for DYRK1A protein.

DYRK1A protein inhibitors derived from 7-azaindoles substituted at the 3-position by amino-pyrimidines have also been prepared by Meijer et al. (J. Med. Chem 2008, 51, 737-751; WO2008129152). These meriolins have $IC_{50}$ values on DYRK1A protein on the order of about several tens of nM. On the other hand, their lack of selectivity for this specific protein is a problem, as these compounds prove to be cytotoxic.

One of the principal disadvantages of compounds of the prior art known to inhibit DYRK1A protein is in general their low affinity and/or selectivity for DYRK1A protein and/or their cytotoxicity.

3,5-Diaryl-7-azaindoles were recently prepared by Hong et al. (Journal of Medicinal Chemistry 2012, 55, 5337-5349). Numerous compounds were prepared and the ability thereof to inhibit tyrosine kinase was evaluated. Among the compounds synthesized, the most effective is able to inhibit tyrosine kinase A with an $IC_{50}$ of about 1 nM.

Other 3,5-diaryl-7-azaindoles able to modulate or inhibit protein kinase activity have been described in patent applications WO 2007/106236 and WO 2008/124849. The inhibitory capacity of these 3,5-diaryl-7-azaindoles was tested on kinases involved in cell and tumor development, such as Abelson tyrosine kinases (c-Abl), Met receptor tyrosine kinases (MET) and Aurora-2, for which they have an $IC_{50}$ sometimes much lower than 500 nM.

Thus, known 3,5-diaryl-7-azaindoles of the prior art have a remarkable inhibitory activity on kinases involved in cell growth. Since cytotoxic compounds cannot be used to treat pathologies such as Alzheimer's disease or Down's syndrome, it was believed that compounds having a structure similar to that of 3,5-diaryl-7-azaindoles described in the prior art could not be used to inhibit DYRK1A protein selectively.

There is, however, a need for novel DYRK1A protein inhibitors specific for this kinase and not exhibiting cytotoxicity, particularly neurotoxicity.

Surprisingly, the Inventors discovered that the 3,5-diaryl-7-azaindoles according to the present invention are able to inhibit DYRK1A protein with low $IC_{50}$ values, are selective for this kinase and have little or no cytotoxicity.

The present invention thus relates to compounds of formula (I) below and to pharmaceutically acceptable salts, solvates and hydrates thereof or prodrugs thereof:

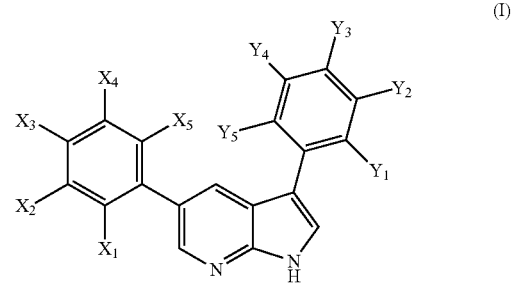

(I)

wherein:
$X_1$-$X_5$ independently of one another are H, F, Cl, Br, $OR_1$ or $SR_2$, preferably H, F, $OR_1$ or $SR_2$,
$Y_1$-$Y_5$ independently of one another are H, F, Cl, Br, $OR_3$ or $SR_4$, preferably H, F, $OR_3$ or $SR_4$, where
$R_1$ and $R_3$ independently of one another represent H; ($C_1$-$C_6$)-alkyl, particularly methyl; acyl, particularly acetyl; optionally substituted aralkyl, particularly benzyl; or optionally substituted aryl; preferably H or methyl, $R_2$ and $R_4$ independently of one another represent H; $(C_1-C_6)$-alkyl, particularly methyl; acyl, particularly acetyl; optionally substituted aralkyl, particularly benzyl; or optionally substituted aryl; preferably H or methyl, one to three radicals among $X_1-X_5$ are different from H, one to three radicals among $Y_1-Y_5$ are different from H, and at least one radical among radicals $X_1-X_5$ and $Y_1-Y_5$ different from H represents F, OH or SH, preferably OH, for use in the treatment of cognitive disorders associated with Down's syndrome.

Advantageously, at least one radical among radicals $X_1-X_5$ different from H is F, OH or SH, preferably OH and at least one radical among radicals $Y_1-Y_5$ different from H is F, OH or SH, preferably OH.

In the compounds according to the present invention, radicals $X_1-X_5$ different from H are preferably F or $OR_1$ and radicals $Y_1-Y_5$ different from H are preferably F or $OR_3$. Advantageously, $R_1$ and $R_3$ independently of one another represent H, methyl, acetyl or benzyl.

In the present invention, by "pharmaceutically acceptable" is meant that which can be used in the preparation of a pharmaceutical composition and is generally safe, non-toxic and neither biologically nor otherwise undesirable and is acceptable for veterinary as well as human pharmaceutical use.

By "pharmaceutically acceptable salts, solvates and hydrates" of a compound is meant in the present invention salts, solvates and hydrates that are pharmaceutically acceptable, as defined herein, and that have the desired pharmacological activity of the parent compound. Such salts comprise:

(1) acid addition salts formed with inorganic acids such as hydrochloric acid, hydrobromic acid, sulfuric acid, nitric acid, phosphoric acid and the like; or formed with organic acids such as acetic acid, benzenesulfonic acid, benzoic acid, acid camphorsulfonic, citric acid, ethane-sulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalene-sulfonic acid, propionic acid, salicylic acid, succinic acid, dibenzoyl-L-tartaric acid, tartaric acid, p-toluenesulfonic acid, trimethylacetic acid, trifluoroacetic acid and the like; and (2) salts formed when an acidic proton present in the parent compound either is replaced by a metal ion, for example an alkaline metal ion ($Na^+$, $K^+$ or $Li^+$, for example), an alkaline-earth metal ion (such as $Ca^{2+}$ or $Mg^{2+}$) or an aluminum ion; or coordinates with an organic or inorganic base. Acceptable organic bases comprise diethanolamine, ethanolamine, N-methylglucamine, triethanolamine, tromethamine and the like. Acceptable inorganic bases comprise aluminum hydroxide, calcium hydroxide, potassium hydroxide, sodium carbonate and sodium hydroxide.

By "halogen" is meant, in the context of the present invention, a bromine, chlorine, iodine or fluorine atom.

By "$(C_1-C_6)$-alkyl" is meant, in the context of the present invention, a saturated linear or branched hydrocarbon chain comprising 1 to 6 carbon atoms, particularly methyl, ethyl, n-propyl, isopropyl, n-butyl, isobutyl, sec-butyl, tert-butyl, n-pentyl, n-hexyl groups.

By "aryl" is meant, in the context of the present invention, an optionally substituted aromatic hydrocarbon group preferably comprising 6 to 10 carbon atoms and comprising one or more joined rings, such as, for example, a phenyl or naphthyl group. Advantageously, it is phenyl.

When the aryl group is substituted, it may advantageously be substituted with one or more groups selected from a halogen atom, preferably a fluorine atom, a $(C_1-C_6)$alkyl, $(C_1-C_6)$alkoxy, aryl, $N_3$, $NO_2$, $NH_2$, or $-NH-((C_1-C_6)$ alkyl) group; preferably selected from a halogen atom, a $(C_1-C_6)$alkyl, $(C_1-C_6)$alkoxy or aryl group.

By "aralkyl" is meant, in the context of the present invention, an aryl group, as defined above, bonded to the molecule via a $(C_1-C_6)$alkyl chain, as defined above.

By "acyl" is meant, in the context of the present invention, a $(C_1-C_6)$-alkyl or aryl group as defined above, bonded to the rest of the molecule via a carbonyl (CO) group. In particular, it may be an acetyl or benzoyl group.

By "N-protecting group" is meant, in the context of the present invention, any substituent that protects the NH group against undesirable reactions, such as the N-protecting groups described in Greene, "Protective Groups in Organic Synthesis," (John Wiley & Sons, New York (1981)) and in Harrison et al., "Compendium of Synthetic Organic Methods," Vols. 1 to 8 (J. Wiley & Sons, 1971 to 1996). N-protecting groups comprise, the protected amine functional group included, carbamates, amides, sulfonamides, N-benzyl derivatives, N-silyl derivatives, mono-alkylaminopropargylamine derivatives and N-heteroatom derivatives.

By "O-protecting group" is meant, in the context of the present invention, any substituent that protects the hydroxyl or carboxyl group, that is, a reactive oxygen atom, against undesirable reactions, such as the O-protecting groups described in Greene, "Protective Groups in Organic Synthesis," (John Wiley & Sons, New York (1981)) and in Harrison et al., "Compendium of Synthetic Organic Methods," Vols. 1 to 8 (J. Wiley & Sons, 1971 to 1996). O-protecting groups comprise substituted or unsubstituted methyl or alkyl ethers, for example, methoxymethyl, benzyloxymethyl, 2-methoxyethoxymethyl, 2-(trimethylsilyl)ethoxymethyl, t-butyl, benzyl and triphenylmethyl, benzyl ethers (substituted or unsubstituted), tetrahydropyranyl ethers, allyl ethers, substituted ethyl ethers, for example, 2,2,2-trichloroethyl, silyl ethers or alkylsilyl ethers, for example, trimethylsilyl (TMS), t-butyldimethylsilyl (TBDMS or TBS) and t-butyldiphenylsilyl, heterocycle ethers; and esters prepared by reaction of the hydroxyl group with a carboxylic acid for example, tert-butyl, benzyl or methyl esters, carbonates, in particular benzyl or haloalkyl carbonate, acetate, propionate, benzoate and the like.

By "S-protecting group" is meant, in the context of the present invention, any substituent that protects the thiol (SH) group against undesirable reactions, such as the S-protecting groups described in Greene, "Protective Groups in Organic Synthesis," (John Wiley & Sons, New York (1981)). S-protecting groups comprise benzyl ethers (substituted or unsubstituted), for example p-methoxybenzyl or p-nitrobenzyl, trityl ethers, thioacetates, thioacetals and thioethers.

By "deprotection" is meant, in the context of the present invention, the process by which a protecting group is removed once the selective reaction is completed. Certain protecting groups may be preferred over others by virtue of their convenience or their relative ease of removal.

By "prodrug" is meant, in the context of the present invention, a compound that is administered in an inactive (or less active) form and that is metabolized in vivo, particularly by the action of enzymes or of gastric acid, in an active (or more active) form. The use of a prodrug improves in particular the physicochemical parameters of a molecule, such as solubility, and the pharmacokinetics (vectorization, bioavailability, etc.), in order to promote its assimilation by an organism after administration. In particular, when a molecule bears a hydroxy (OH) group, the prodrug will result in particular from the acylation or phosphorylation of this hydroxy group.

In certain compounds of formula (I), only one of the radicals among $Y_1$-$Y_5$ is different from H. Advantageously, the radical among $Y_1$-$Y_5$ different from H is $Y_1$, $Y_2$ or $Y_3$, in particular $Y_2$ or $Y_3$ and preferably $Y_3$.

In other compounds of formula (I), two of the radicals among $Y_1$-$Y_5$ are different from H. Advantageously, the two radicals among $Y_1$-$Y_5$ different from H are $Y_1$ and $Y_3$ or $Y_2$ and $Y_3$ and preferably $Y_2$ and $Y_3$.

In yet other compounds of formula (I), three of the radicals among $Y_1$-$Y_5$ are different from H. Advantageously, the three radicals among $Y_1$-$Y_5$ different from H are $Y_2$, $Y_3$ and $Y_5$ or $Y_2$, $Y_3$ and $Y_4$.

Advantageously, at least $Y_3$ is different from H.

In certain compounds of formula (I), only one radical among $X_1$-$X_5$ is different from H. Advantageously, the radical among $X_1$-$X_5$ different from H is $X_1$, $X_2$ or $X_3$, in particular $X_1$ or $X_3$ and preferably $X_3$.

In other compounds of formula (I), two of the radicals among $X_1$-$X_5$ are different from H. Advantageously, the two radicals among $X_1$-$X_5$ different from H are $X_1$ and $X_3$, $X_1$ and $X_2$, $X_1$ and $X_4$ or $X_2$ and $X_3$, in particular $X_2$ and $X_3$, $X_1$ and $X_4$ or $X_1$ and $X_3$ and preferably $X_1$ and $X_3$ or $X_2$ and $X_3$.

In yet other compounds of formula (I), three of the radicals among $X_1$-$X_5$ are different from H. Advantageously, the three radicals among $X_1$-$X_5$ that are not a hydrogen atom are $X_2$, $X_3$ and $X_5$ or $X_2$, $X_3$ and $X_4$.

Advantageously, at least one of $X_1$, $X_3$ or $X_4$ is different from H, preferably $X_3$.

In a first particular embodiment according to the invention, $X_1$ and $Y_3$ are simultaneously different from H, $X_1$ represents F, Cl, Br, $OR_1$ or $SR_2$, in particular F or $OR_1$ and $Y_3$ represents F, Cl, Br, $OR_3$ or $SR_4$, in particular F or $OR_3$. In particular, $X_1$ and $Y_3$ are simultaneously different from H and $X_2$, $X_3$, $X_4$, $X_5$, $Y_1$, $Y_2$, $Y_4$ and $Y_5$ simultaneously represent hydrogen.

In certain compounds of formula (I) according to this embodiment, $X_1$, $Y_2$ and $Y_3$ are simultaneously different from H, $X_1$ represents F, Cl, Br, $OR_1$ or $SR_2$, in particular F or $OR_1$ and $Y_2$ and $Y_3$ independently represent F, Cl, Br, $OR_3$ or $SR_4$, in particular F or $OR_3$. In particular, $X_2$, $X_3$, $X_4$, $X_5$, $Y_1$, $Y_4$ and $Y_5$ simultaneously represent hydrogen.

In other compounds of formula (I) according to this embodiment, $X_1$, $X_3$ and $Y_3$ are simultaneously different from H, $X_1$ and $X_3$ independently represent F, Cl, Br, $OR_1$ or $SR_2$, in particular F or $OR_1$, and $Y_3$ represents F, Cl, Br, $OR_3$ or $SR_4$, in particular F or $OR_3$. In particular, $X_2$, $X_4$, $X_5$, $Y_1$, $Y_2$, $Y_4$ and $Y_5$ simultaneously represent hydrogen.

In a second particular embodiment according to the invention, $X_3$ and $Y_3$ are different from H, $X_3$ represents F, Cl, Br, $OR_1$ or $SR_2$, in particular F or $OR_1$, and $Y_3$ represents F, Cl, Br, $OR_3$ or $SR_4$, in particular F or $OR_3$. In particular, $X_1$, $X_2$, $X_4$, $X_5$, $Y_1$, $Y_2$, $Y_4$ and $Y_5$ simultaneously represent hydrogen.

In certain compounds of formula (I) according to this embodiment, $X_3$, $Y_2$ and $Y_3$ are different from H, $X_3$ represents F, Cl, Br, $OR_1$ or $SR_2$, in particular F or $OR_1$, and $Y_2$ and $Y_3$ independently represent F, Cl, Br, $OR_3$ or $SR_4$, in particular F or $OR_3$. In particular, $X_1$, $X_2$, $X_4$, $X_5$, $Y_1$, $Y_4$ and $Y_5$ simultaneously represent hydrogen.

In a third particular embodiment according to the invention, $X_2$, $X_3$ and $Y_3$ are different from H, $X_2$ and $X_3$ independently represent F, Cl, Br, $OR_1$ or $SR_2$, in particular F or $OR_1$, and $Y_3$ represents F, Cl, Br, $OR_3$ or $SR_4$, in particular F or $OR_3$. In particular, $X_1$, $X_4$, $X_5$, $Y_1$, $Y_2$, $Y_4$ and $Y_5$ simultaneously represent hydrogen.

In a fourth particular embodiment according to the invention, $X_2$, $X_3$, $Y_2$ and $Y_3$ are different from H, $X_2$ and $X_3$ independently represent F, Cl, Br, $OR_1$ or $SR_2$, in particular F or $OR_1$, and $Y_2$ and $Y_3$ independently represent F, Cl, Br, $OR_3$ or $SR_4$, in particular F or $OR_3$. Preferentially, $X_1$, $X_4$, $X_5$, $Y_1$, $Y_4$ and $Y_5$ simultaneously represent hydrogen.

The present invention also relates to a method for the prevention and/or treatment of cognitive disorders associated with Down's syndrome comprising the administration of an effective amount of at least one compound of formula (I), pharmaceutically acceptable salts, solvates, hydrates thereof or prodrugs thereof as defined above to a patient in need thereof.

The present invention also relates to the use of at least one compound of formula (I), pharmaceutically acceptable salts, solvates, hydrates thereof or prodrugs thereof as defined above for the manufacture of a medication intended for the prevention and/or treatment of cognitive disorders associated with Down's syndrome.

The present invention also relates to novel compounds of formula (I') as defined below, and to pharmaceutically acceptable salts, solvates, hydrates thereof or prodrugs thereof:

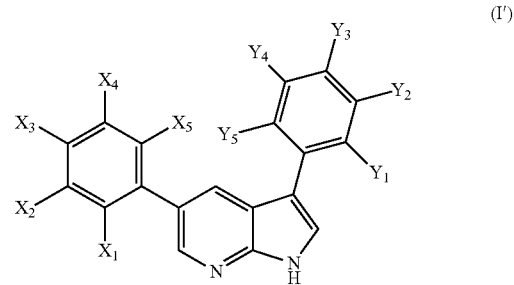

(I')

wherein:
$X_1$, $X_2$, $X_4$, $X_5$, $Y_1$, $Y_2$, $Y_4$ and $Y_5$ independently of one another are H, F, Cl, Br, OH or SH, preferably H, F, OH or SH,
$X_3$ is F, OH or SH, preferably OH,
$Y_3$ is F, OH or SH, preferably OH, and
one to two groups among radicals $X_1$, $X_2$, $X_4$ and $X_5$ are different from H and/or one to two groups among radicals $Y_1$, $Y_2$, $Y_4$ and $Y_5$ are different from H.

Thus, in the compounds of formula (I'), one of the 3- and 5-position aromatic rings of the 7-azaindole is substituted with at least one F, Cl, Br, OH or SH group, preferably F, OH or SH, in addition to radicals $X_3$ and $Y_3$. One of the 3- and 5-position aromatic rings of the 7-azaindole is thus di- or tri-substituted and the second aromatic ring mono-, di- or tri-substituted.

The number and position of radicals $X_1$-$X_5$ and $Y_1$-$Y_5$ and the embodiments as defined for the compounds of formula (I) are applicable to the compounds of formula (I').

In particular, in the compounds of formula (I'), at least one radical among $X_1$-$X_5$ represents OH and at least one radical among $Y_1$-$Y_5$ represents OH. Advantageously, the radical among $X_1$-$X_5$ representing OH is $X_2$ or $X_3$ and the radical among $Y_1$-$Y_5$ representing OH is $Y_2$ or $Y_3$. Preferably, $X_3$ and $Y_3$ are OH.

Advantageously, in the compounds of formula (I'), all the radicals among $X_1$-$X_5$ different from H independently of one another are F or OH and preferably OH and all the radicals among $Y_1$-$Y_5$ different from H independently of one another are F or OH and preferably OH.

The compounds of formula (I') are in particular selected from the following compounds:

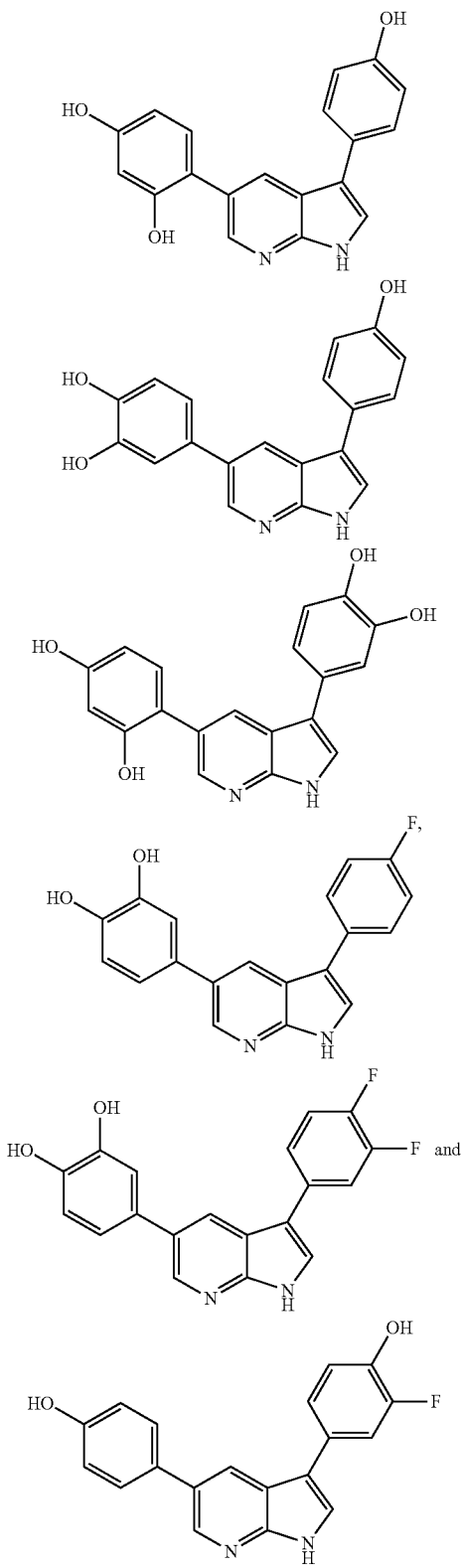

The present invention also relates to compounds of formula (I') and to pharmaceutically acceptable salts, solvates, hydrates thereof or prodrugs thereof as defined above for use as a medication.

The present invention also relates to compounds of formula (I') and to pharmaceutically acceptable salts, solvates, hydrates thereof or prodrugs thereof as defined above for use in the prevention and/or treatment of cognitive disorders associated with dysfunction of DYRK1A protein, in particular in the prevention and/or treatment of cognitive disorders associated with Down's syndrome or Alzheimer's disease.

The present invention also relates to a method for the prevention and/or treatment of cognitive disorders associated with dysfunction of DYRK1A protein, in particular a method for the prevention and/or treatment of cognitive disorders associated with Down's syndrome or Alzheimer's disease, comprising the administration of an effective amount of at least one compound of formula (I'), pharmaceutically acceptable salts, solvates, hydrates thereof or prodrugs thereof as defined above to a patient in need thereof.

The present invention also relates to the use of a compound of formula (I'), pharmaceutically acceptable salts, solvates, hydrates thereof or prodrugs thereof as defined above for the manufacture of a medication, in particular intended for the treatment of cognitive disorders associated with dysfunction of DYRK1A protein, in particular for the prevention and/or treatment of cognitive disorders associated with Down's syndrome or Alzheimer's disease.

Another subject matter of the present invention is a pharmaceutical composition comprising at least one compound of formula (I'), pharmaceutically acceptable salts, solvates, hydrates thereof or prodrugs thereof as defined above and a pharmaceutically acceptable excipient.

The pharmaceutical composition comprising at least one compound of formula (I') is intended for the treatment of cognitive disorders associated with dysfunction of DYRK1A protein, in particular for the prevention and/or treatment of cognitive disorders associated with Down's syndrome or Alzheimer's disease.

The pharmaceutical compositions according to the invention may be formulated for parenteral (subcutaneous, intraperitoneal, intramuscular, intravenous or intrathecal, for example), oral, sublingual, transdermal, local or rectal administration, intended for mammals, including humans. The dosing regimen varies according to the treatment and to the ailment concerned.

In the pharmaceutical compositions of the present invention, the active ingredient may be administered in unit forms of administration, in mixture with conventional pharmaceutical carriers, to animals or to humans.

Suitable oral unit forms of administration comprise tablets, capsules, powders, granules and oral solutions or suspensions, and parenteral administration forms, in particular intraperitoneal forms.

When a solid composition in tablet form is prepared, the principal active ingredient is mixed with a pharmaceutical carrier such as gelatin, starch, lactose, magnesium stearate, talc, gum arabic or analogs. The tablets may be coated with sucrose or other suitable materials or they may be treated such that they have sustained or delayed activity and that they continuously release a predetermined amount of active ingredient.

A capsule preparation is obtained by mixing the active ingredient with a diluent and by pouring the mixture obtained into soft or hard capsules.

A preparation in syrup or elixir form may contain the active ingredient together with a sweetener, an antiseptic, and a flavoring agent and a suitable colorant.

Water-dispersible powders or granules may contain the active ingredient in mixture with dispersion or wetting agents, or suspension agents, and with flavor correctors or sweeteners.

For parenteral administration, aqueous suspensions, isotonic saline solutions or sterile injectable solutions containing pharmacologically compatible dispersants and/or wetting agents are used.

The active ingredient may also be formulated in microcapsule form, optionally with one or more additive carriers.

Another subject matter of the present invention is a method for the preparation of a compound of formula (I') as defined above or one of the pharmaceutically acceptable salts, solvates and hydrates thereof comprising the steps of:

(a) reaction between a compound of formula (II'):

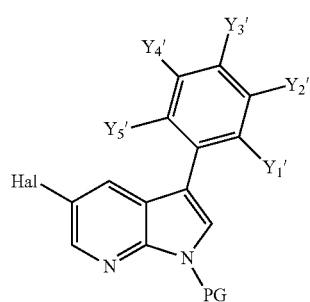

(II')

and a compound of formula (III'):

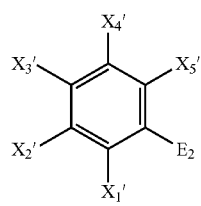

(III')

wherein:
PG represents an N-protecting group,
Hal represents a halogen atom, in particular bromine, or an OSO$_2$CF$_3$ group,
E$_2$ represents a boronic acid B(OH)$_2$ or a derivative thereof,
radicals X$_3'$ and Y$_3'$ are F, OPG$_1$ or SPG$_2$, where PG$_1$ represents an O-protecting group and PG$_2$ represents an S-protecting group,
radicals X$_1$, X$_2$, X$_4$, X$_5$, Y$_1$, Y$_2$, Y$_4$ and Y$_5$ independently of one another are H, F, Cl, Br, OPG$_1$ or SPG$_2$,
PG$_1$ represents an O-protecting group and PG$_2$ represents an S-protecting group, to yield a compound of formula (IV'):

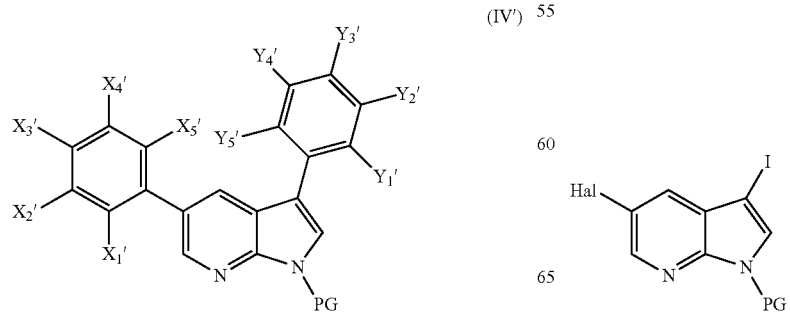

(IV')

(b) deprotection of the N-PG group of the compound of formula (IV') and the OPG$_1$ and SPG$_2$ groups to yield a compound of formula (I'), (c) optionally salification, solvation or hydration to yield a pharmaceutically acceptable salt, solvate or hydrate of a compound of formula (I').

Preferred N-protecting groups according to the present invention are tosylamides such as benzenesulfonamide, 4-nitrobenzenesulfonamide and para-toluenesulfonamide and carbamates such as t-butyloxycarbonyl (Boc), benzyloxycarbonyl (Cbz), benzyl carbamates.

Preferred O-protecting groups according to the invention are optionally substituted benzyl ethers such as 4-methoxybenzyl; the methoxymethyl group and alkyl ethers such as methyl ether and esters such as an acyl group and preferably an acetyl group.

Preferred S-protecting groups according to the invention are optionally substituted benzyl thioethers such as 4-methoxybenzyl; thioesters such as an acyl group and preferably an acetyl group.

Advantageously, this reaction is carried out in the presence of a catalyst containing a transition metal such as Pd, Ni, Cu and preferably Pd. Preferred catalysts are complexes of palladium, of nickel or of copper and preferably of palladium. For example, the catalyst may be Pd(PPh$_3$)$_4$ or Pd(OAc)$_2$.

The reaction is carried out at a temperature between 20 and 150° C., preferably between 80 and 110° C.

The solvents used to carry out this reaction are aromatic solvents such as toluene, alcohols such as ethanol, propanol and isopropanol and ketones such as acetone. Preferably, the reaction is carried out in a mixture of an aromatic solvent and an alcohol, in particular in a toluene/ethanol mixture.

The reaction may be carried out in the presence of a base. Examples of bases are carbonates such as Na$_2$CO$_3$ or K$_2$CO$_3$, and alkaline metal hydroxides such as NaOH or KOH.

The deprotection step may be carried out according to methods well-known to the skilled person such as those described in Greene, "Protective Groups in Organic Synthesis," (John Wiley & Sons, New York (1981)) and in Harrison et al., "Compendium of Synthetic Organic Methods," Vols. 1 to 8 (J. Wiley & Sons, 1971 to 1996).

The compounds of formula (I') may be prepared from a 5-halo-3-iodo-azaindole according to the method shown in the following diagram:

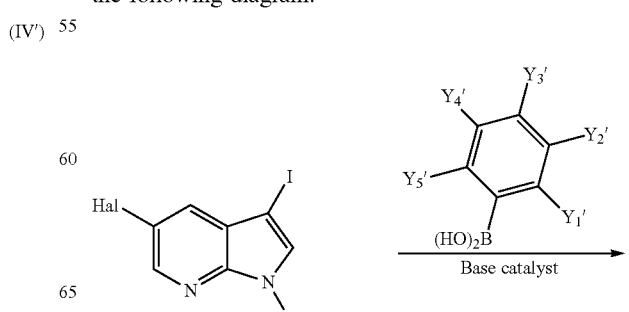

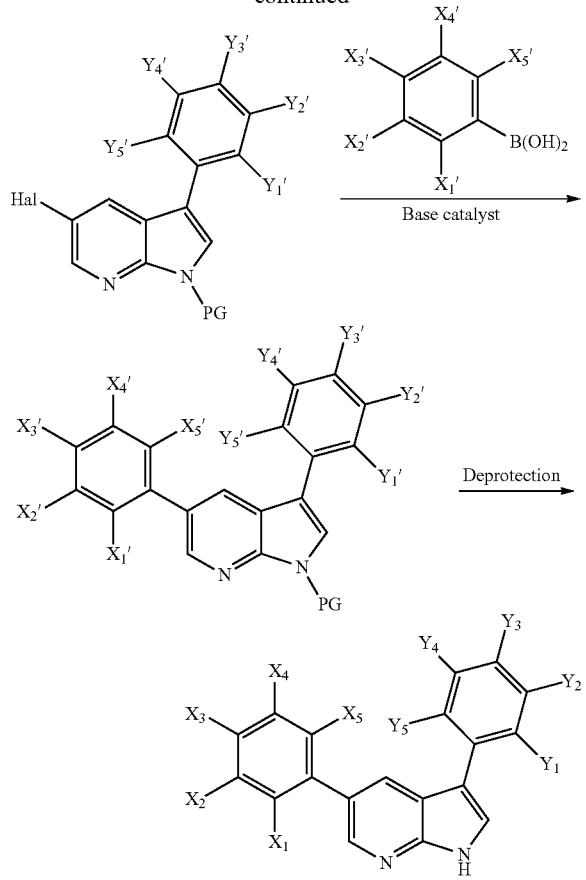

The method according to the invention comprises the steps of:
- (a) protection of the 1-indole nitrogen with an N-protecting group,
- (b) reaction between the 3-iodo-5-halo-azaindole and an aryl-boronic acid or a derivative thereof in the presence of a metal catalyst,
- (c) reaction between the 3-aryl-5-halo-azaindole and an aryl-boronic acid or a derivative thereof in the presence of a metal catalyst,
- (d) deprotection of the N-PG group and optionally the $OPG_1$ or $SPG_2$ groups to yield a compound of formula (I') as defined above,
- (e) optionally salification, solvation or hydration to yield a pharmaceutically acceptable salt, solvate or hydrate of a compound of formula (I').

Finally, a subject matter of the present invention is a method for assaying the phosphorylating activity of DYRK1A kinase. This method is based on the separation, detection and quantification of a peptide substrate of the enzyme and the phosphorylated product thereof. This substrate bears a fluorescent group which allows sensitive and specific detection of the substrate and the product.

By "unphosphorylated substrate bearing a fluorescent group" is meant in the context of the present invention a molecule which is phosphorylated by DYRK1A enzyme and on which a fluorescent group is grafted.

The term "phosphorylated substrate bearing a fluorescent group" refers in the context of the present invention to the product obtained after phosphorylation by DYRK1A enzyme of the unphosphorylated substrate bearing a fluorescent group.

Under the conditions of the assay method, DYRK1A protein transforms the unphosphorylated substrate bearing a fluorescent group into a phosphorylated substrate bearing a fluorescent group. The proportion of unphosphorylated substrate bearing a fluorescent group and phosphorylated substrate bearing a fluorescent group over a given period of time depends on the phosphorylating activity of DYRK1A protein. In the presence of inhibitor, the phosphorylating activity of DYRK1A protein decreases as the efficacy of this inhibitor increases. Determination of the proportion of unphosphorylated substrate bearing a fluorescent group and phosphorylated substrate bearing a fluorescent group over a given period of time thus measures the phosphorylating activity of DYRK1A protein.

The assay method comprises the steps of:
- (a) Contacting DYRK1A protein with the unphosphorylated substrate bearing a fluorescent group to yield the phosphorylated substrate bearing a fluorescent group and the unphosphorylated substrate bearing a fluorescent group,
- (b) Separating the enzyme-phosphorylated substrate bearing a fluorescent group and the unphosphorylated substrate bearing a fluorescent group by means of chromatography, and
- (c) Measuring the proportion unphosphorylated substrate bearing a fluorescent group/phosphorylated substrate bearing a fluorescent group by means of a fluorescence detector.

The unphosphorylated substrate is in particular a peptide or a protein. It may be a peptide having the sequence ISGRLSPIMTEQ (SEQ ID NO: 1) or KKISGRLSPIMTEQ (SEQ ID NO: 2) as described in Woods, Y. et al. Biochem. J. 355, 597 (2001); Woods, Y. et al. Biochem. J. 355, 609 (2001); Klumpp, M. et al. J. Biomol. Screen. 11, 617 (2006).

The fluorescent group is preferably selected from the group consisting of fluorescein isothiocyanate (FITC), fluorescein, p-nitroaniline (pNA) and biotin.

Preparation of the unphosphorylated substrate bearing a fluorescent group is carried out according to methods well-known to the skilled person.

Advantageously, the unphosphorylated substrate bearing a fluorescent group is the peptide fluorescein-KKISGRL-SPIMTEQ.

Separation of the unphosphorylated substrate bearing a fluorescent group and the phosphorylated substrate bearing a fluorescent group may be carried out by chromatography. Separation is in particular carried out by ultra-fast liquid chromatography (UFLC). Preferably, the enzyme-phosphorylated substrate bearing a fluorescent group is separated from the unphosphorylated substrate bearing a fluorescent group by means of chromatography on a hydrophobic $C_8$-$C_{18}$ column coupled to a UFLC apparatus and a fluorescence detector.

FIG. 1 shows the results obtained in vivo with the compounds according to the invention on the phosphorylation state of two DYRK1A downstream targets in signaling pathways.

FIG. 1a: The y-axis represents the ratio of phosphorylated GSK (pGSK) to unphosphorylated GSK (GSK) measured using a slot-blot technique. The x-axis represents compounds tested on control animals (WT) or on animals of an animal model of trisomy for DYRK1A gene (TG).

Figure 1B:
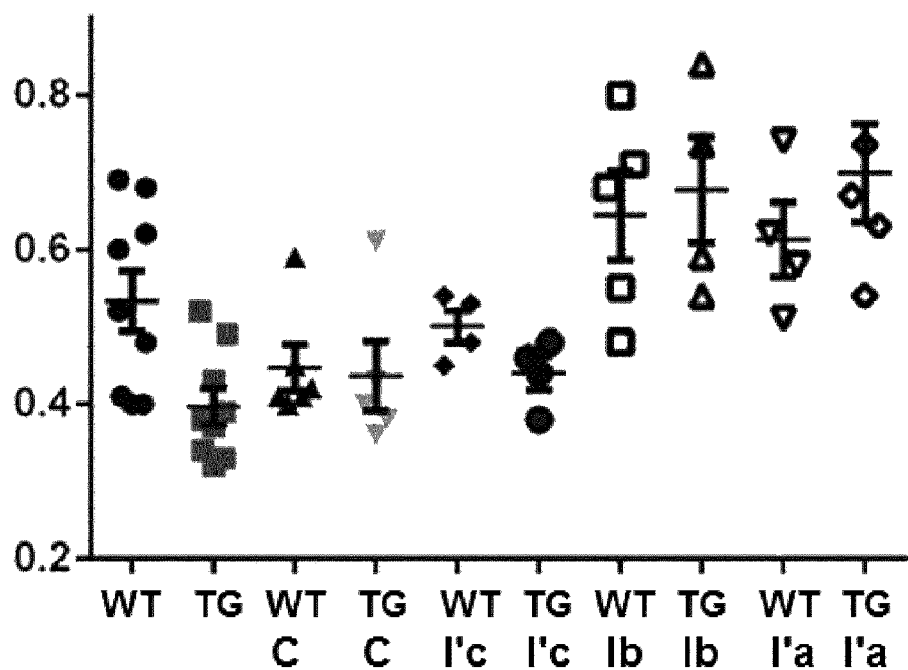

FIG. 1b: The y-axis represents the ratio of phosphorylated CAMKII (pCAMKII) to unphosphorylated CAMKII (CAMKII) measured using a slot-blot technique. The x-axis represents compounds tested on control animals (WT) or on animals of an animal model of trisomy for DYRK1A gene (TG).

The present invention will be better understood in the light of the following non-limiting examples.

EXAMPLES

Example 1

Synthesis of 3,5-diarylazaindoles

Preparation of 3-phenyl-5-(2-hydroxyphenyl-1H-pyrrolo[2,3-b]pyridine (Compound A) is provided as an example.

3-iodo-5-bromo-1H-pyrrolo[2,3-b]-pyridine (commercial product)

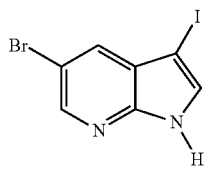 [SMILES: Brc1cnc2[nH]cc(I)c2c1]

To a solution of 5-bromo-1H-pyrrolo[2,3-b]-pyridine (commercial product, 1 g, 5.10 mmol) in 200 ml of $CH_2Cl_2$ is added KOH (145 mg, 2.55 mmol) at room temperature. After 30 minutes, N-iodosuccinimide (1.2 g, 5.10 mmol) is added and the solution is stirred for 15 hours, neutralized with saturated $Na_2S_2O_3$ solution and extracted several times with $CH_2Cl_2$. The organic phases are combined, dried on $MgSO_4$ and concentrated under reduced pressure. The expected product is obtained with a quantitative yield and used in the following step without additional purification.

$^1$H NMR (DMSO-$d_6$, 300 MHz) δ 12.34 (s, 1H), 8.31 (d, J=2.1 Hz, 1H), 7.86 (d, J=2.1 Hz, 1H), 7.30 (s, 1H);
$^{13}$C NMR (DMSO-$d_6$, 75 MHz) δ 146.5, 143.8, 132.5, 129.9, 123.8, 111.5, 53.6.
HRMS (ESI+) calculated for $C_7H_4{}^{79}BrIN_2[M+H]^+$ 322.8681. found 322.8682, HRMS (ESI+) calculated for $C_7H_4{}^{81}BrIN_2[M+H]^+$ 324.8660. found 324.8670.
IR (cm$^{-1}$): v 3118, 2821, 1638.

3-iodo-5-bromo-1-(phenylsulfonyl)-1H-pyrrolo[2,3-b]pyridine

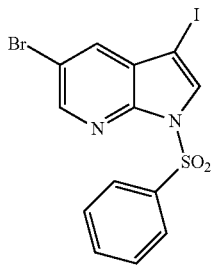 [SMILES: O=S(=O)(c1ccccc1)n1cc(I)c2cc(Br)cnc21]

To a solution of 3-iodo-5-bromo-1H-pyrrolo[2,3-b]-pyridine (500 mg, 1.55 mmol) in $CH_2Cl_2$ (4.1 ml) are added 60% sodium hydride (186 mg, 4.66 mmol) and benzyltriethylammonium chloride (8 mg, 0.03 mmol) under argon at 0° C. After 30 minutes, benzenesulfonyl chloride (240 μl, 1.86 mmol) is added at 0° C. and the mixture is stirred at room temperature for 2 hours. The mixture is neutralized with water and extracted several times with $CH_2Cl_2$. The organic phases are combined, dried on $MgSO_4$ and concentrated under reduced pressure. The residue is precipitated with methanol and the resulting solid filtered to yield the expected product in the form of a pink solid with 97% yield.

$^1$H NMR (CDCl$_3$, 500 MHz) δ 8.46 (d, J=2.0 Hz, 1H), 8.19 (d, J=8.0 Hz, 2H), 7.88 (s, 1H), 7.82 (d, J=2.5 Hz, 1H), 7.64-7.61 (m, 1H), 7.54-7.51 (m, 2H);
$^{13}$C NMR (CDCl$_3$, 75 MHz) δ 146.7, 144.7, 137.6, 134.6, 132.5, 131.2, 129.2, 128.2, 126.7, 116.0, 60.6.
HRMS (ESI+) calculated for $C_{13}H_9N_2O_2S^{79}Br[M+H]^+$ 462.8613. found 462.8605, HRMS (ESI+) calculated for $C_{13}H_9N_2O_2S^{81}Br[M+H]^+$ 464.8592. found 464.8596.
IR (cm$^{-1}$): v 2851, 1613, 1370.

3-phenyl-5-bromo-1-(phenylsulfonyl)-1H-pyrrolo[2,3-b]pyridine

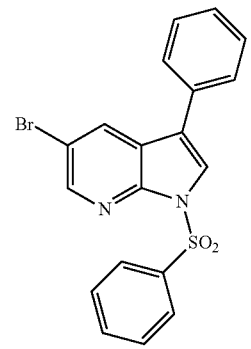 [SMILES: O=S(=O)(c1ccccc1)n1cc(-c2ccccc2)c2cc(Br)cnc21]

To a solution of 3-iodo-5-bromo-1-(phenylsulfonyl)-1H-pyrrolo[2,3-b]pyridine (250 mg, 0.54 mmol) in a 3:1 toluene/ethanol mixture (17 ml) are added benzene boronic acid (65 mg, 0.54 mmol), $K_2CO_3$ (1.6 ml of 2 M solution in water, 3.20 mmol) and Pd(PPh$_3$)$_4$ (1.5 mol %) and the reaction is heated at 110° C. for 3.5 hours under argon.

The mixture is cooled to room temperature, concentrated under a vacuum and redissolved in a water/$CH_2Cl_2$ mixture. The aqueous phase is extracted several times with $CH_2Cl_2$ and the combined organic phases are dried on $MgSO_4$. The solvent is evaporated under reduced pressure and the residue purified by flash chromatography on silica gel (100% $CH_2Cl_2$) to yield the purified product in the form of a white solid with 89% yield.

$^1$H NMR (CDCl$_3$, 300 MHz) δ 8.50 (d, J=2.1 Hz, 1H), 8.25-8.20 (m, 3H), 7.90 (s, 1H), 7.64-7.36 (m, 8H);
$^{13}$C NMR (CDCl$_3$, 75 MHz) δ 145.7, 145.6, 137.9, 134.3, 131.8, 131.1, 129.1, 129.0, 128.0, 127.9, 127.3, 123.9, 123.1, 119.8, 115.5.
HRMS (ESI+) calculated for $C_{19}H_{14}N_2O_2S^{79}Br$ $[M+H]^+$ 412.9959. found 412.9969, HRMS (ESI+) calculated for $C_{19}H_{14}N_2O_2S^{81}Br$ $[M+H]^+$ 414.9939. found 412.9958.
IR (cm$^{-1}$): v 2919, 1605, 1383.

3-phenyl-5-(4-methoxyphenyl)-1-(phenylsulfonyl)-1H-pyrrolo[2,3-b]pyridine

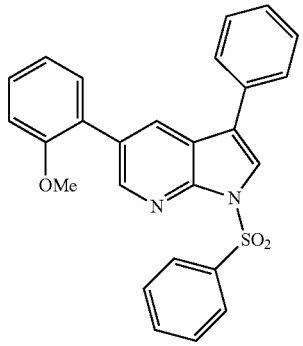 [SMILES: COc1ccccc1-c1cnc2c(c1)c(-c1ccccc1)cn2S(=O)(=O)c1ccccc1]

To a solution of 3-phenyl-5-bromo-1-(phenylsulfonyl)-1H-pyrrolo[2,3-b]pyridine (309 mg, 0.75 mmol) in a 3:1 toluene/ethanol mixture (24 ml) are added 2-methoxy-benzene boronic acid (125 mg, 0.83 mmol), $K_2CO_3$ (2.4 ml of 2 M solution in water, 4.5 mmol), $Pd(PPh_3)_4$ (1.5 mol %), and the mixture is heated at 85° C. for 2 hours under argon. The mixture is cooled to room temperature, concentrated under a vacuum and redissolved in a water/$CH_2Cl_2$ mixture. The aqueous phase is extracted several times with $CH_2Cl_2$ and the combined organic phases are dried on $MgSO_4$. The solvent is evaporated under reduced pressure and the residue purified by flash chromatography on silica gel (100% $CH_2Cl_2$) to yield the purified product in the form of a colorless oil with a yield of 98%.

$^1$H NMR (CDCl$_3$, 300 MHz) δ 8.66 (d, J=2.1 Hz, 1H), 8.31-8.25 (m, 3H), 7.92 (s, 1H), 7.65-7.58 (m, 3H), 7.55-7.45 (m, 4H), 7.41-7.30 (m, 3H), 7.1-7.0 (m, 2H), 3.81 (s, 3H);

$^{13}$C NMR (CDCl$_3$, 75 MHz) δ 156.5, 146.5, 146.3, 138.4, 134.0, 132.7, 131.0, 130.1, 129.6, 129.3, 129.0, 129.0, 128.0, 127.6, 127.4, 127.3, 122.7, 121.1, 121.0, 120.6, 111.2, 55.5.

HRMS (ESI+) calculated for $C_{26}H_{21}N_2O_3S$ [M+H]$^+$ 441.1273. found 441.1273.

IR (cm$^{-1}$): ν 2925, 1601, 1385.

3-phenyl-5-(2-methoxyphenyl)-1H-pyrrolo[2,3-b]pyridine

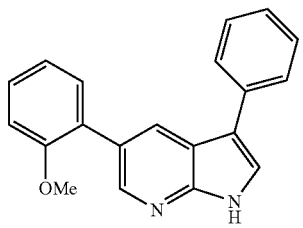 [SMILES: COc1ccccc1-c1cnc2[nH]cc(-c3ccccc3)c2c1]

To a solution of 3-phenyl-5-(2-methoxyphenyl)-1-(phenylsulfonyl)-1H-pyrrolo[2,3-b]pyridine (374 mg, 0.85 mmol) in methanol (2.3 ml) is added NaOH (260 μl of 2 N solution in water, 0.51 mmol). The mixture is heated at 80° C. for 1 hour and then cooled at room temperature.

The mixture is cooled to room temperature, concentrated under a vacuum and redissolved in a water/$CH_2Cl_2$ mixture. The aqueous phase is extracted several times with $CH_2Cl_2$ and the combined organic phases are dried on $MgSO_4$. The solvent is evaporated under reduced pressure and the residue purified by flash chromatography on silica gel ($CH_2Cl_2$/MeOH, gradient 100/0 to 98:2) to yield the purified product in the form of a yellow solid with 42% yield.

$^1$H NMR (CDCl$_3$, 500 MHz) δ 11.50 (br s, 1H), 8.61 (s, 1H), 8.43 (s, 1H), 7.70 (d, J=8.0 Hz, 2H), 7.62 (s, 1H), 7.49-7.38 (m, 4H), 7.33-7.30 (m, 1H), 7.13-7.10 (m, 1H), 7.06 (br d, J=8.0 Hz, 1H), 3.87 (s, 3H);

$^{13}$C NMR (CDCl$_3$, 75 MHz) δ 156.7, 148.3, 143.9, 135.1, 131.3, 129.4 (2CH), 128.9, 128.8, 128.7, 127.1 (2CH+C), 126.1, 122.7, 121.0, 118.3, 116.5, 111.3, 55.6.

HRMS (ESI+) calculated for $C_{20}H_{17}N_2O$ [M+H]$^+$ 301.1341. found 301.1337.

IR (cm$^{-1}$): ν 3124, 2833, 1599.

UPLC R$_t$=4.35 min; area 100%.

3-phenyl-5-(2-hydroxyphenyl)-1H-pyrrolo[2,3-b]pyridine (A)

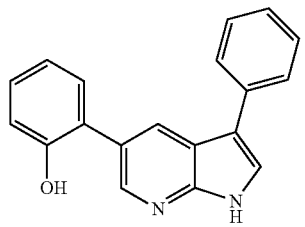 [SMILES: Oc1ccccc1-c1cnc2[nH]cc(-c3ccccc3)c2c1]

To a solution of 3-phenyl-5-(2-methoxyphenyl)-1H-pyrrolo[2,3-b]pyridine (113 mg, 0.38 mmol) in $CH_2Cl_2$ (325 μl) is added BBr$_3$ (1.1 ml of 1 N solution in $CH_2Cl_2$, 1.13 mmol). The reaction mixture is stirred for 15 hours at room temperature and neutralized at 0° C. with methanol. The solvent is evaporated under reduced pressure and the residue purified by preparative thin-layer chromatography ($CH_2Cl_2$/MeOH 94:6) to yield the expected product in the form of a white solid with a yield of 34%.

$^1$H NMR (CD$_3$OD, 300 MHz) δ 8.42 (s, 1H), 8.32 (d, J=2.1 Hz, 1H), 7.63 (br d, J=6.9 Hz, 2H), 7.58 (s, 1H) 7.40-7.35 (m, 2H), 7.31-7.28 (m, 1H), 7.24-7.14 (m, 2H), 6.95-6.89 (m, 2H);

$^{13}$C NMR (CD$_3$OD, 75 MHz) δ 155.6, 148.5, 144.5, 136.3, 131.9, 130.3, 129.8 (2CH), 129.7, 128.6, 127.9 (2CH), 127.6, 127.0, 124.4, 121.2, 119.6, 117.4, 117.0.

HRMS (ESI+) calculated for $C_{19}H_{15}N_2O$ [M+H]$^+$ 287.1184. found 287.1188.

IR (cm$^{-1}$): ν 3267, 2869, 1602, 1262.

UPLC R$_t$=3.67 min; area 100%.

The others compounds were prepared according to the same method from suitable aryl-boronic acids.

3-phenyl-5-phenyl-1H-pyrrolo[2,3-b]pyridine (B)

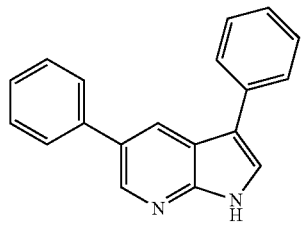 [SMILES: c1ccc(-c2cnc3[nH]cc(-c4ccccc4)c3c2)cc1]

¹H NMR (CDCl₃, 300 MHz) δ 10.93 (s, 1H), 8.65 (d, J=1.8 Hz, 1H), 8.45 (d, J=1.8 Hz, 1H), 7.73-7.6 (m, 4H), 7.54 (s, 1H), 7.52-7.46 (m, 4H), 7.43-7.31 (m, 2H);

¹³C NMR (CDCl₃, 75 MHz) δ 148.7, 142.4, 139.5, 134.9, 130.3, 129.0 (2CH), 128.9 (2CH), 127.5 (2CH), 127.2 (2CH), 127.1, 126.9, 126.3, 122.9, 118.6, 116.8.

HRMS (ESI+) calculated for $C_{19}H_{15}N_2$ [M+H]⁺ 271.1235. found 271.1226.

IR (cm⁻¹): v. 3136, 2884, 1602. UPLC $R_t$=4.51 min; area 100%.

3-phenyl-5-(4-hydroxyphenyl)-1H-pyrrolo[2,3-b]pyridine (C)

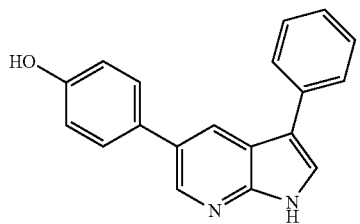 [SMILES: Oc1ccc(-c2cnc3[nH]cc(-c4ccccc4)c3c2)cc1]

¹H NMR (CD₃OD, 300 MHz) δ 8.40 (d, J=2.1 Hz, 1H), 8.32 (d, J=2.1 Hz, 1H), 7.64 (br d, J=6.9 Hz, 2H), 7.61 (s, 1H) 7.48-7.39 (m, 4H), 7.28-7.25 (m, 1H), 6.89 (br d, J=8.7 Hz, 2H);

¹³C NMR (CD₃OD, 75 MHz) δ 158.2, 148.9, 142.4, 136.3, 131.8 (2CH), 131.3 (2CH), 129.9 (2CH), 129.4 (2CH), 127.9 (2CH), 127.1, 127.0, 124.7, 120.0, 117.3, 116.8 (2CH).

HRMS (ESI+) calculated for $C_{19}H_{15}N_2O$ [M+H]⁺ 287.1184. found 287.1188.

IR (cm⁻¹): v 3142, 2890, 1602, 1259.

UPLC $R_t$=3.44 min; area 100%.

3-phenyl-5-(3-hydroxyphenyl)-1H-pyrrolo[2,3-b]pyridine (D)

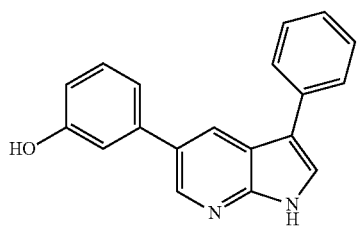 [SMILES: Oc1cccc(-c2cnc3[nH]cc(-c4ccccc4)c3c2)c1]

¹H NMR (CD₃OD, 300 MHz) δ 8.45 (d, J=2.1 Hz, 1H), 8.38 (d, J=2.1 Hz, 1H), 7.69-7.65 (m, 3H), 7.46-7.41 (m, 2H), 7.31-7.24 (m, 2H), 7.13-7.08 (m, 2H), 6.80 (dd, J=8.1 Hz, 1.5 Hz, 1H);

¹³C NMR (CD₃OD, 75 MHz) 159.1, 149.4, 142.7, 142.0, 136.3, 131.3, 131.1, 129.9 (2CH), 128.0 (2CH), 127.6, 127.2, 125.0, 120.0, 119.6, 117.5, 115.2, 115.0.

HRMS (ESI+) calculated for $C_{19}H_{15}N_2O$ [M+H]⁺ 287.1184. found 287.1182.

IR (cm⁻¹): v 3124, 2919, 1596.

UPLC $R_t$=3.64 min; area 100%.

3-phenyl-5-(3,4-dihydroxyphenyl)-1H-pyrrolo[2,3-b]pyridine (E)

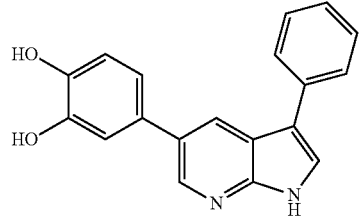 [SMILES: Oc1ccc(-c2cnc3[nH]cc(-c4ccccc4)c3c2)cc1O]

¹H NMR (DMSO-d₆, 300 MHz) δ 11.90 (br s, 1H), 9.01 (s, 1H), 9.00 (s, 1H), 8.44 (d, J=1.8 Hz, 1H), 8.27 (d, J=2.1 Hz, 1H), 7.87 (s, 1H), 7.76 (d, J=7.5 Hz, 2H), 7.48-7.43 (m, 2H), 7.28-7.23 (m, 1H), 7.09 (s, 1H), 7.01 (d, J=8.1 Hz, 1H), 6.84 (d, J=8.1 Hz, 1H);

¹³C NMR (DMSO-d₆, 75 MHz) δ 148.2, 145.6, 144.8, 141.6, 135.1, 131.3, 130.4, 130.3, 129.2, 128.9, 126.3, 125.6, 124.4, 124.3, 118.0, 117.2, 114.4.

HRMS (ESI+) calculated for $C_{19}H_{15}N_2O_2$ [M+H]⁺ 303.1134. found 303.1143.

IR (cm⁻¹): v 3112, 2830, 1601, 1254.

UPLC $R_t$=3.74 min; area 100%.

3-phenyl-5-(2,4-dihydroxyphenyl)-1H-pyrrolo[2,3-b]pyridine (F)

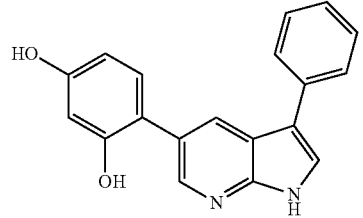 [SMILES: Oc1ccc(-c2cnc3[nH]cc(-c4ccccc4)c3c2)c(O)c1]

¹H NMR (CD₃OD, 300 MHz) δ 8.39 (s, 2H), 7.69 (br d, J=9.3 Hz, 2H), 7.62 (s, 1H), 7.45-7.39 (m, 2H), 7.28-7.22 (m, 1H), 7.15 (d, J=8.1 Hz, 1H), 6.45-6.41 (m, 2H);

¹³C NMR (CD₃OD, 75 MHz) δ 159.2, 156.5, 148.3, 144.5, 136.5, 132.4, 130.1, 129.9 (2CH), 128.9, 127.9 (2CH), 127.0, 124.3, 119.7, 119.3, 117.3, 108.4, 104.1.

HRMS (ESI+) calculated for $C_{19}H_{15}N_2O_2$ [M+H]⁺ 303.1134. found 303.1124.

IR (cm⁻¹): v 3252, 2833, 1605, 1259. UPLC $R_t$=2.94 min; area 100%.

3-(3-methoxyphenyl)-5-(3-methoxyphenyl)-1H-pyrrolo[2,3-b]pyridine (G)

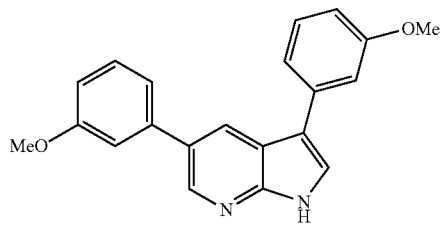 [SMILES: COc1cccc(-c2cnc3[nH]cc(-c4cccc(OC)c4)c3c2)c1]

¹H NMR (CDCl₃, 300 MHz) δ 10.64 (br s, 1H), 8.63 (d, J=2.1 Hz, 1H), 8.44 (d, J=2.1 Hz, 1H), 7.62 (s, 1H), 7.45-7.38 (m, 2H), 7.31-7.18 (m, 5H), 6.97-6.87 (m, 2H), 3.91 (s, 3H), 3.90 (s, 3H); ¹³C NMR (CDCl₃, 75 MHz) δ 160.1, 160.0, 148.4, 142.1, 140.9, 136.1, 130.2, 130.0 (2CH), 127.2, 123.2, 120.0, 119.7, 118.7, 116.8, 113.4, 113.1, 112.5, 111.7, 55.4, 55.3. HRMS (ESI+) calculated for C₂₁H₁₉N₂O₂ [M+H]⁺ 331.1447. found 331.1443.

IR (cm⁻¹): ν 3109, 2830, 1607, 1207.

UPLC R$_t$=4.39 min; area 100%.

3-(3-hydroxyphenyl)-5-(3-hydroxyphenyl)-1H-pyrrolo[2,3-b]pyridine (Ia)

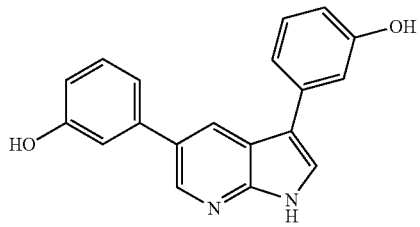 [SMILES: Oc1cccc(-c2cnc3[nH]cc(-c4cccc(O)c4)c3c2)c1]

¹H NMR (CD₃OD, 300 MHz) δ 8.45 (s, 1H), 8.42 (d, J=2.1 Hz, 1H), 7.64 (s, 1H), 7.32-7.24 (m, 2H), 7.19-7.08 (m, 4H), 6.82-6.70 (m, 2H);

¹³C NMR (CD₃OD, 75 MHz) δ 159.1, 158.9, 149.3, 142.6, 142.0, 137.6, 131.2, 131.1, 131.0, 127.7, 124.9, 119.9, 119.6, 119.3, 117.5, 115.2, 115.0, 114.7, 114.2.

HRMS (ESI+) calculated for C₁₉H₁₅N₂O₂ [M+H]⁺ 303.1134. found 303.1127.

IR (cm⁻¹): ν 3314, 3014, 1599, 1275.

UPLC R$_t$=2.91 min; area 100%.

3-(4-methoxyphenyl)-5-(4-methoxyphenyl)-1H-pyrrolo[2,3-b]pyridine (H)

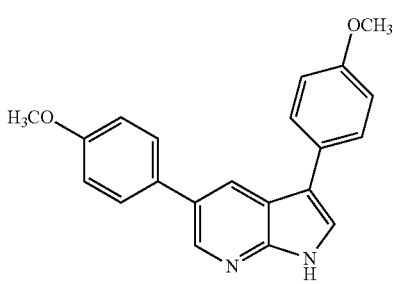 [SMILES: COc1ccc(-c2cnc3[nH]cc(-c4ccc(OC)cc4)c3c2)cc1]

Mp 190° C.

¹H NMR (CDCl₃, 300 MHz) δ 10.60 (br s, 1H), 8.58 (d, J=2.1 Hz, 1H), 8.33 (d, J=2.1 Hz, 1H), 7.63-7.57 (m, 4H), 7.51 (s, 1H), 7.03 (d, J=8.4 Hz, 4H) 3.89 (s, 3H), 3.88 (s, 3H);

¹³C NMR (CDCl₃, 75 MHz) δ 159.1, 158.3, 148.3, 142.1, 132.1, 129.8, 128.5 (2CH), 128.3 (2CH), 127.5, 126.4, 122.1, 118.7, 116.4, 114.5 (2CH), 114.4 (2CH), 55.4, 55.3.

HRMS (ESI−) calculated for C₂₁H₁₇N₂O₂ [M−H]⁻ 329.1290. found 329.1282.

IR (cm⁻¹): ν 3143, 2853, 1606.

UPLC R$_t$=4.20 min; area 100%.

3-(4-hydroxyphenyl)-5-(4-hydroxyphenyl)-1H-pyrrolo[2,3-b]pyridine (Ib)

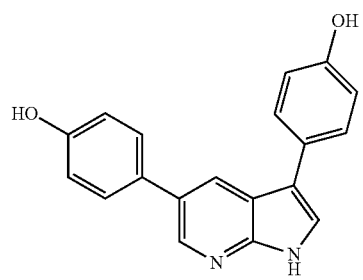 [SMILES: Oc1ccc(-c2cnc3[nH]cc(-c4ccc(O)cc4)c3c2)cc1]

Mp 150-160° C.

¹H NMR (CD₃OD, 300 MHz) δ 8.38 (d, J=1.5 Hz, 1H), 8.29 (d, J=2.1 Hz, 1H), 7.52-7.46 (m, 5H), 6.92-6.88 (m, 4H);

¹³C NMR (CD₃OD, 75 MHz) δ 158.1, 157.1, 148.8, 142.2, 132.0, 131.1, 129.4 (2CH), 129.3 (2CH), 127.7, 127.2, 123.9, 120.2, 117.5, 116.9 (2CH), 116.8 (2CH).

HRMS (ESI+) calculated for C₁₉H₁₅N₂O₂ [M+H]⁺ 303.1134. found 303.1127.

IR (cm⁻¹): ν 3136, 2937, 1601, 1257.

UPLC R$_t$=2.47 min; area 100%.

3-(4-methoxyphenyl)-5-(2,4-dimethoxyphenyl)-1H-pyrrolo[2,3-b]pyridine (J)

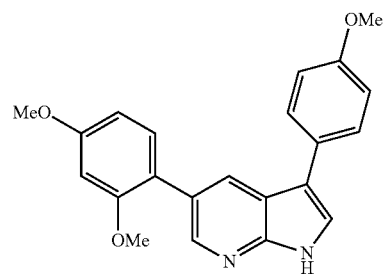 [SMILES: COc1ccc(-c2c[nH]c3ncc(-c4ccc(OC)cc4OC)cc23)cc1]

Mp 90° C.

¹H NMR (CDCl₃, 300 MHz) δ 10.21 (br s, 1H), 8.50 (s, 1H), 8.31 (d, J=2.1 Hz, 1H), 7.61-7.58 (m, 2H), 7.48 (s, 1H), 7.32-7.29 (m, 1H), 7.03-7.00 (m, 2H), 6.65-6.61 (m, 2H), 3.89 (s, 3H), 3.87 (s, 3H), 3.83 (s, 3H);

¹³C NMR (CDCl₃, 75 MHz) δ 160.5, 158.3, 157.6, 147.5, 143.9, 131.6, 129.3, 128.3 (2CH), 127.5, 126.9, 121.7, 121.4, 118.4, 116.5, 114.4 (2CH), 104.8, 99.1, 55.6, 55.5, 55.3.

HRMS (ESI+) calculated for C₂₂H₂₁N₂O₃ [M+H]⁺ 361.1552. found 361.1557.

IR (cm⁻¹): ν 3312, 1998, 1616.

UPLC R$_t$=4.08 min; area 100%.

3-(4-hydroxyphenyl)-5-(2,4-dihydroxyphenyl)-1H-pyrrolo[2,3-b]pyridine (I'a)

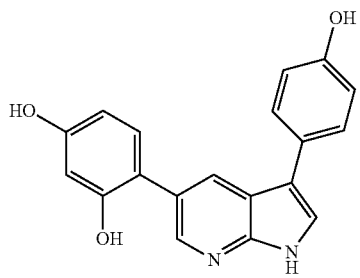 [SMILES: Oc1ccc(-c2c[nH]c3ncc(-c4ccc(O)cc4O)cc23)cc1]

Mp 201-210° C.
$^1$H NMR (CD$_3$OD, 300 MHz) δ 8.34 (d, J=2.1 Hz, 1H), 8.31 (d, J=2.1 Hz, 1H), 7.48-7.51 (m, 2H), 7.47 (s, 1H), 7.14 (d, J=8.1 Hz, 1H), 6.88 (dd, J=8.4 Hz, 2.1 Hz, 2H), 6.44 (s, 1H), 6.41-6.45 (m, 1H);
$^{13}$C NMR (CD$_3$OD, 75 MHz) δ 159.1, 157.0, 156.5, 148.3, 144.4, 132.5, 130.0, 129.2 (2CH), 128.6, 127.9, 123.2, 119.8, 119.4, 117.4, 116.7 (2CH), 108.4, 104.1.
HRMS (ESI+) calculated for C$_{19}$H$_{15}$N$_2$O$_3$ [M+H]$^+$ 319.1083. found 319.1087.
IR (cm$^{-1}$): ν 3189, 3008, 1605, 1260.
UPLC R$_t$=2.10 min; area 100%.

3-(4-methoxyphenyl)-5-(3,4-di methoxyphenyl)-1H-pyrrolo[2,3-b]pyridine (K)

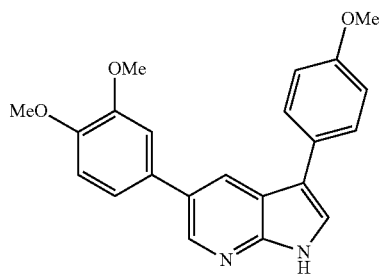 [SMILES: COc1ccc(-c2c[nH]c3ncc(-c4ccc(OC)c(OC)c4)cc23)cc1]

$^1$H NMR (CDCl$_3$, 300 MHz) δ 9.85 (br s, 1H), 8.29 (d, J=2.1 Hz, 1H), 8.08 (d, J=2.1 Hz, 1H), 7.33 (d, J=8.7 Hz, 2H), 7.24 (s, 1H), 6.93.6.86 (m, 2H), 6.79-6.72 (m, 3H), 3.71 (s, 3H), 3.69 (s, 3H), 3.61 (s, 3H);
$^{13}$C NMR (CDCl$_3$, 75 MHz) δ 158.5, 149.4, 148.7, 147.5, 141.5, 132.3, 130.2, 128.4 (2CH), 127.1, 127.0, 122.3, 119.8, 119.0, 116.7, 114.5 (2CH), 111.7, 110.9, 56.1, 56.0, 55.4.
HRMS (ESI−) calculated for C$_{22}$H$_{19}$N$_2$O$_3$ [M−H]$^-$ 359.1396. found 359.1389.
IR (cm$^{-1}$): ν 3112, 2833, 1571, 1241.
UPLC R$_t$=3.85 min; area 100%.

3-(4-hydroxyphenyl)-5-(3,4-dihydroxyphenyl)-1H-pyrrolo[2,3-b]pyridine (I'b)

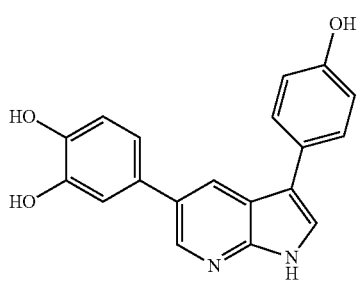 [SMILES: Oc1ccc(-c2c[nH]c3ncc(-c4ccc(O)c(O)c4)cc23)cc1]

Mp 275° C. (degradation).
$^1$H NMR (CD$_3$OD, 300 MHz) δ 8.37 (d, J=2.1 Hz, 1H), 8.27 (d, J=2.1 Hz, 1H), 7.52-7.49 (m, 3H), 7.08 (d, J=2.1 Hz, 1H), 7.00-6.97 (m, 1H), 6.91-6.86 (m, 3H);
$^{13}$C NMR (CD$_3$OD, 75 MHz) δ 157.1, 148.9, 146.8, 146.1, 142.2, 132.6, 131.2, 129.3 (2CH), 127.7, 127.1, 123.8, 120.2, 119.8, 117.5, 117.0, 116.8 (2CH), 115.3.
HRMS (ESI−) calculated for C$_{19}$H$_{13}$N$_2$O$_3$ [M−H]$^-$ 317.0926. found 317.0936.
IR (cm$^{-1}$): ν 3264, 3017, 1601, 1257.
UPLC R$_t$=2.22 min; area 100%.

3-(3,4-dimethoxyphenyl)-5-(3,4-dimethoxyphenyl)-1H-pyrrolo[2,3-b]pyridine (L)

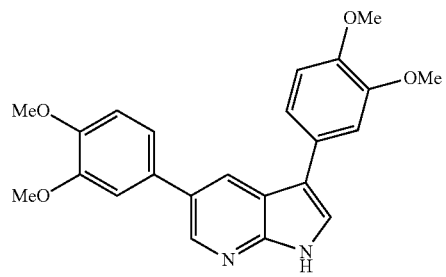 [SMILES: COc1ccc(-c2cnc3[nH]cc(-c4ccc(OC)c(OC)c4)c3c2)cc1OC]

$^1$H NMR (CDCl$_3$, 300 MHz) δ 10.10 (br s, 1H), 8.54 (s, 1H), 8.42 (s, 1H), 7.54 (s, 1H), 7.24-7.11 (m, 4H), 7.01 (d, J=8.1 Hz, 2H), 3.98 (s, 3H), 3.97 (s, 3H), 3.96 (s, 6H);
$^{13}$C NMR (CDCl$_3$, 75 MHz) δ 149.4 (2C), 148.8, 148.2, 146.9, 140.9, 132.0, 130.3, 127.4, 127.3, 122.7, 119.8, 119.7, 119.4, 117.1, 111.9, 111.8, 110.9, 110.8, 56.1 (4CH$_3$).
HRMS (ESI+) calculated for C$_{23}$H$_{23}$N$_2$O$_4$ [M+H]$^+$ 391.1658. found 391.1663.
IR (cm$^{-1}$): ν 3124, 2833, 1604, 1247.
UPLC R$_t$=3.52 min; area 100%.

3-(3,4-dihydroxyphenyl)-5-(3,4-dihydroxyphenyl)-1H-pyrrolo[2,3-b]pyridine (I'c)

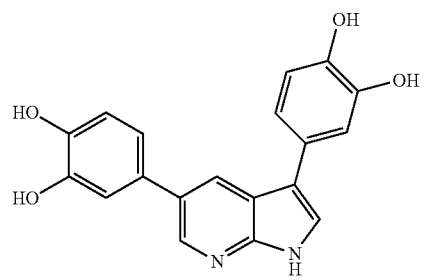 [SMILES: Oc1ccc(-c2cnc3[nH]cc(-c4ccc(O)c(O)c4)c3c2)cc1O]

Mp 190° C.
$^1$H NMR (CD$_3$OD, 300 MHz) δ 8.37 (d, J=2.1 Hz, 1H), 8.31 (d, J=2.1 Hz, 1H), 7.49 (s, 1H), 7.14 (d, J=2.1 Hz, 1H), 7.09 (d, J=2.1 Hz, 1H), 7.03-6.97 (m, 2H), 6.89 (d, J=3.9 Hz, 1H), 6.86 (d, J=3.9 Hz, 1H);
$^{13}$C NMR (CD$_3$OD, 75 MHz) δ 148.8, 146.8, 146.6, 146.0, 145.1, 142.2, 132.6, 131.2, 128.3, 127.2, 123.8, 120.1, 119.8, 119.6, 117.6, 117.0 (2CH), 115.3 (2CH).
HRMS (ESI+) calculated for C$_{19}$H$_{15}$N$_2$O$_4$ [M+H]$^+$ 335.1032. found 335.1038.
IR (cm$^{-1}$): ν 3172, 3047, 1596, 1270.
UPLC R$_t$=1.99 min; area 100%.

3-(3,4-dimethoxyphenyl)-5-(2,4-dimethoxyphenyl)-1H-pyrrolo[2,3-b]pyridine (M)

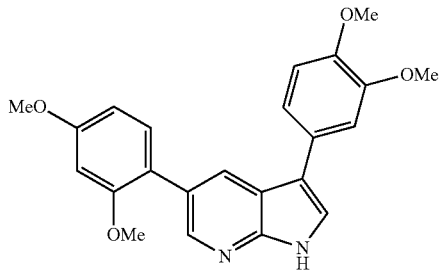 [SMILES: COc1ccc(-c2cnc3[nH]cc(-c4ccc(OC)c(OC)c4)c3c2)c(OC)c1]

$^1$H NMR (CDCl$_3$, 300 MHz) δ 10.70 (br s, 1H), 8.51 (s, 1H), 8.33 (d, J=2.1 Hz, 1H), 7.51 (s, 1H), 7.33-7.29 (m, 1H), 7.24-7.18 (m, 2H), 6.98 (d, J=8.4 Hz, 1H), 6.65-6.60 (m, 2H), 3.97 (s, 3H), 3.94 (s, 3H), 3.88 (s, 3H), 3.83 (s, 3H);

$^{13}$C NMR (CDCl$_3$, 75 MHz) δ 160.5, 157.6, 149.3, 147.8, 147.6, 143.9, 131.5, 129.2, 128.0, 126.9, 122.0, 121.3, 119.5, 118.4, 116.5, 111.8, 110.8, 104.8, 99.1, 56.0, 55.9, 55.6, 55.5.

HRMS (ESI+) calculated for C$_{23}$H$_{23}$N$_2$O$_4$ [M+H]$^+$ 391.1658. found 391.1657.

IR (cm$^{-1}$): ν 3124, 2934, 1611, 1248.

UPLC R$_t$=3.74 min; area 100%.

3-(3,4-dimethoxyphenyl)-5-(2,5-dimethoxyphenyl)-1H-pyrrolo[2,3-b]pyridine (N)

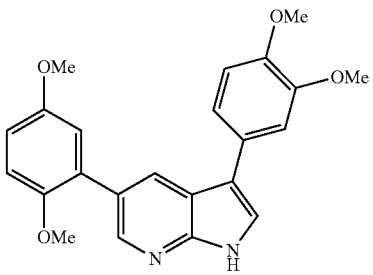

$^1$H NMR (CDCl$_3$, 300 MHz) δ 10.89 (br s, 1H), 8.56 (d, J=1.5 Hz, 1H), 8.39 (d, J=1.8 Hz, 1H), 7.54 (s, 1H), 7.25-7.18 (m, 2H), 7.00-6.97 (m, 3H), 6.93-6.88 (m, 1H), 3.97 (s, 3H), 3.94 (s, 3H), 3.84 (s, 3H), 3.79 (s, 3H);

$^{13}$C NMR (CDCl$_3$, 75 MHz) δ 153.9, 150.9, 149.3, 147.9, 147.8, 143.8, 129.5, 129.3, 127.8, 126.8, 122.1, 119.5, 118.4, 117.1, 116.6, 113.1, 112.6, 111.8, 110.7, 56.3, 56.0, 55.9, 55.8.

HRMS (ESI+) calculated for C$_{23}$H$_{23}$N$_2$O$_4$ [M+H]$^+$ 391.1658. found 391.1648.

IR (cm$^{-1}$): ν 3130, 2830, 1582, 1245.

UPLC R$_t$=3.80 min; area 100%.

3-(3,4-dihydroxyphenyl)-5-(2,4-dihydroxyphenyl)-1H-pyrrolo[2,3-b]pyridine (I'd)

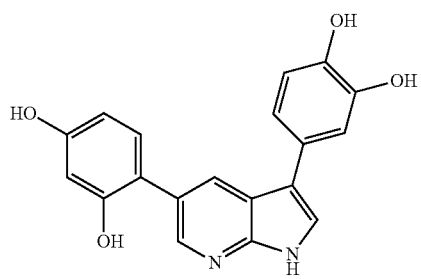 [SMILES: Oc1ccc(-c2cnc3[nH]cc(-c4ccc(O)c(O)c4)c3c2)c(O)c1]

Mp 197° C.

$^1$H NMR (CD$_3$OD, 300 MHz) δ 8.36-8.33 (m, 2H), 7.54 (s, 1H), 7.16-7.13 (m, 2H), 7.02-6.98 (m, 1H), 6.85 (br d, J=8.1 Hz, 1H), 6.45-6.40 (m, 2H);

$^{13}$C NMR (CD$_3$OD, 75 MHz) δ 159.1, 156.5, 148.3, 146.6, 145.0, 144.4, 132.5, 130.0, 128.6, 128.5, 123.2, 119.8, 119.7, 119.5, 117.5, 116.9, 115.3, 108.4, 104.1.

HRMS (ESI+) calculated for C$_{19}$H$_{15}$N$_2$O$_4$ [M+H]$^+$ 335.1032. found 335.1025.

IR (cm$^{-1}$): ν 3136, 2842, 1604, 1259.

UPLC R$_t$=1.89 min; area 100%.

3-(3,4-dihydroxyphenyl)-5-(2,5-dihydroxyphenyl)-1H-pyrrolo[2,3-b]pyridine (I'e)

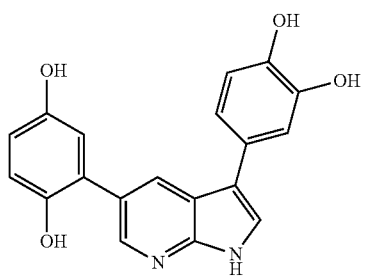 [SMILES: Oc1ccc(O)c(-c2cnc3[nH]cc(-c4ccc(O)c(O)c4)c3c2)c1]

Mp 180° C.

$^1$H NMR (CD$_3$OD, 300 MHz) δ 8.40 (m, 2H), 7.48 (s, 1H), 7.13 (d, J=2.1 Hz, 1H), 7.01 (dd, J=8.1 Hz, 2.1 Hz, 1H), 6.87-6.77 (m, 3H), 6.68-6.64 (m, 1H);

$^{13}$C NMR (CD$_3$OD, 75 MHz) δ 151.7, 148.6, 148.4, 146.6, 145.0, 144.3, 130.2, 128.4 (3C), 123.4, 119.7, 119.6, 118.1, 118.0, 117.7, 116.9, 116.1, 115.3.

HRMS (ESI+) calculated for C$_{19}$H$_{15}$N$_2$O$_4$ [M+H]$^+$ 335.1032. found 335.1023.

IR (cm$^{-1}$): ν 3216, 2916, 1605, 1276.

UPLC R$_t$=1.75 min; area 100%.

3-(4-fluorophenyl)-5-(3,4-dimethoxyphenyl)-1H-pyrrolo[2,3-b]pyridine (If)

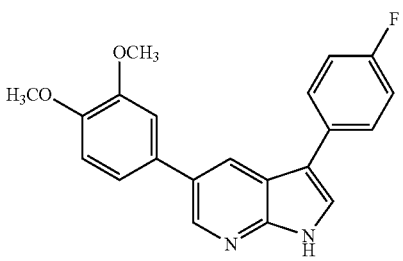 [SMILES: COc1ccc(-c2cnc3[nH]cc(-c4ccc(F)cc4)c3c2)cc1OC]

$^1$H NMR (300 MHz, CDCl$_3$) δ 3.96 (s, 3H), 4.00 (s, 3H), 7.00 (d, J=8.3 Hz, 1H), 7.14-7.21 (m, 4H), 7.56 (s, 1H), 7.61-7.65 (m, 2H), 8.31 (d, J=1.9 Hz, 1H), 8.59 (d, J=2.1 Hz, 1H), 11.0 (s, 1H).

$^{13}$C NMR (75 MHz, CDCl$_3$) δ 56.0, 56.1, 110.9, 111.7, 115.7 (d, J=21.4 Hz, 2C), 115.8, 118.7, 119.9, 123.0, 126.5, 128.6 (d, J=7.7 Hz, 2C), 130.3, 130.8 (d, J=3.3 Hz, 1C), 132.3, 141.9, 148.1, 148.7, 149.4, 160.0 (d, J=245.4 Hz, 1C).

HRMS (ES+) m/z calculated for C$_{21}$H H$_{18}$FN$_2$O$_2$ [M+H]$^+$, 349.1352. found, 349.1357.

IR (cm$^{-1}$) v 3130, 3033, 2904, 1247.

UPLC R$_t$=4.07 min; area 100%.

3-(4-fluorophenyl)-5-(3,4-dihydroxyphenyl)-1H-pyrrolo[2,3-b]pyridine (I'f)

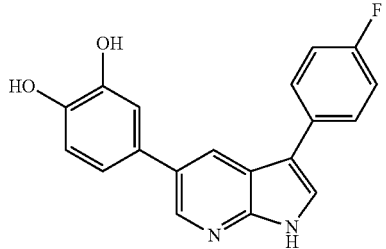 [SMILES: Oc1ccc(-c2cnc3[nH]cc(-c4ccc(F)cc4)c3c2)cc1O]

$^1$H NMR (300 MHz, DMSO) δ 6.83 (d, J=8.1 Hz, 1H), 6.98 (dd, J=8.1, 2.1 Hz, 1H), 7.09 (d, J=2.3 Hz, 1H), 7.24-7.30 (m, 2H), 7.77-7.81 (m, 2H), 7.85 (d, J=2.4 Hz, 1H), 8.24 (d, J=2.1 Hz, 1H), 8.43 (d, J=2.1 Hz, 1H), 8.99 (d, J=3.0 Hz, 2H), 11.90 (s, 1H).

$^{13}$C NMR (75 MHz, DMSO) δ 113.4, 114.4, 115.5 (d, J=21.4 Hz, 2C), 116.1, 117.1, 118.0, 124.3, 128.0 (d, J=7.7 Hz, 2C), 129.2, 130.3, 131.5 (d, J=3.3 Hz, 1C), 141.6, 144.8, 145.7, 148.1, 158.9 (d, J=242.1 Hz, 1C).

HRMS (ES+) m/z calculated for C$_{19}$H$_{14}$FN$_2$O$_2$ [M+H]$^+$, 321.1039. found, 321.1045.

IR (cm$^{-1}$) v 3246, 3044, 2926, 1217.

UPLC R$_t$=3.25 min; area 100%.

3-(3,4-difluorophenyl)-5-(3,4-dimethoxyphenyl)-1H-pyrrolo[2,3-b]pyridine (Ig)

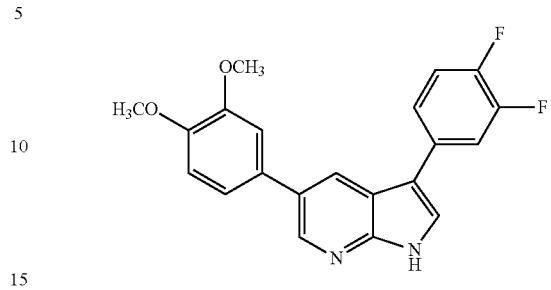

$^1$H NMR (300 MHz, CDCl$_3$) δ 3.96 (s, 3H), 3.99 (s, 3H), 7.00 (d, J=8.1 Hz, 1H), 7.13 (d, J=1.9 Hz, 1H), 7.17 (dd, J=8.3, 1.7 Hz, 1H), 7.22-7.31 (m, 1H), 7.35-7.40 (m, 1H), 7.42-7.50 (m, 1H), 7.58 (s, 1H), 8.32 (d, J=1.7 Hz, 1H), 8.59 (d, J=1.9 Hz, 1H), 11.19 (s, 1H).

$^{13}$C NMR (75 MHz, CDCl$_3$) δ 56.0, 56.1, 110.9, 111.8, 114.9, 115.7 (d, J=17.6 Hz, 1C), 117.7 (d, J=17.0 Hz, 1C), 118.4, 119.9, 122.9-123.0 (m), 123.4, 126.4, 130.6, 131.8-131.9 (m), 132.1, 142.2, 147.4 (dd, J=247.6, 12.6 Hz, 1C), 148.1, 148.8, 148.9 (dd, J=247.6, 12.6 Hz, 1C), 149.4.

HRMS (ES+) m/z calculated for C$_{21}$H$_{17}$F$_2$N$_2$O$_2$ [M+H]$^+$, 367.1258. found, 367.1266.

IR (cm$^{-1}$) v 3128, 3027, 2965, 1268.

UPLC R$_t$=4.24 min; area 100%.

3-(3,4-difluorophenyl)-5-(3,4-dihydroxyphenyl)-1H-pyrrolo[2,3-b]pyridine (I'g)

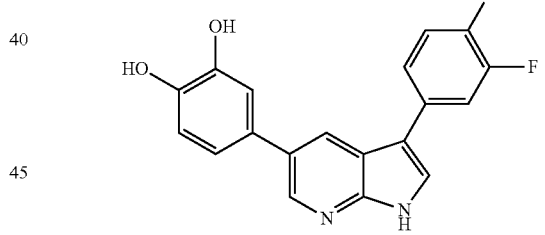

$^1$H NMR (300 MHz, DMSO) δ 6.85 (d, J=8.1 Hz, 1H), 7.05 (d, J=8.3 Hz, 1H), 7.16 (s, 1H), 7.45-7.55 (m, 1H), 7.64-7.68 (m, 1H), 7.83-7.90 (m, 1H), 8.05 (s, 1H), 8.48-8.54 (m, 2H), 12.38 (s, 1H).

$^{13}$C NMR (75 MHz, DMSO) δ 113.7, 115.1, 115.6 (d, J=17.6 Hz, 1C), 116.6, 118.3 (d, J=16.7 Hz, 1C), 118.8, 119.1 (d, J=5.2 Hz, 1C), 123.6, 126.5-126.7 (m), 127.6-127.7 (m), 129.6, 130.1, 132.5, 139.3-139.7 (m), 145.7, 146.2, 146.7 (dd, J=244.5, 12.6 Hz, 1C), 147.0, 148.6 (dd, J=244.5, 12.6 Hz, 1C)

HRMS (ES+) m/z calculated for C$_{19}$H$_{13}$F$_2$N$_2$O$_2$ [M+H]$^+$, 339.0945. found, 339.0932.

IR (cm$^{-1}$) v 3117, 2924, 1269.

UPLC R$_t$=3.43 min; area 100%.

The compounds of formula (Ic) and (I'h) were prepared from 3-(3-fluoro-4-methoxyphenyl)-5-(4-benzyloxyphenyl)-1H-pyrrolo[2,3-b]pyridine.

3-(3-fluoro-4-methoxyphenyl)-5-(4-hydroxyphenyl)-1H-pyrrolo[2,3-b]pyridine

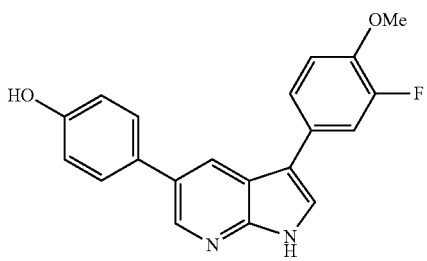 [SMILES: COc1ccc(-c2c[nH]c3ncc(-c4ccc(O)cc4)cc23)cc1F]

$^1$H NMR (300 MHz, DMSO) δ 3.87 (s, 3H), 6.87 (d, J=8.7 Hz, 2H), 7.20 (t, J=8.9 Hz, 1H), 7.55 (d, J=8.5 Hz, 4H), 7.86 (s, 1H), 8.29 (d, J=2.1 Hz, 1H), 8.47 (d, J=1.9 Hz, 1H), 9.69 (s, 1H), 11.93 (s, 1H).
$^{13}$C NMR (75 MHz, DMSO) δ 56.1, 113.2 (d, J=2.2 Hz, 1C), 113.7 (d, J=18.7 Hz, 1C), 114.4 (d, J=1.6 Hz, 1C), 115.9, 117.1, 122.4 (d, J=2.7 Hz, 1C), 124.3, 124.5, 128.2, 128.3 (d, J=7.1 Hz, 1C), 129.0, 129.6, 141.7, 145.1 (d, J=11.0 Hz, 1C), 148.1, 150.3 (d, J=243.2 Hz, 1C), 157.0.
HRMS (ES+) m/z calculated for $C_{20}H_{16}FN_2O_2$ [M+H]$^+$, 335.1196. found, 335.1191.
IR (cm$^{-1}$) ν 3371, 3015, 2931, 1266.
UPLC $R_t$=3.42 min; area 95%.

3-(3-fluoro-4-hydroxyphenyl)-5-(4-hydroxyphenyl)-1H-pyrrolo[2,3-b]pyridine (I'h)

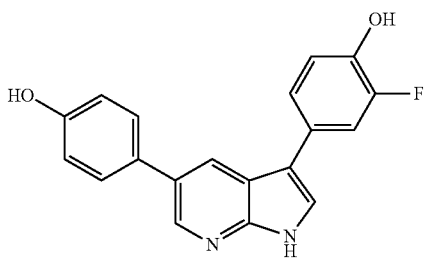 [SMILES: Oc1ccc(-c2cnc3[nH]cc(-c4ccc(O)c(F)c4)c3c2)cc1]

$^1$H NMR (300 MHz, MeOD) δ 6.93-6.96 (m, 2H), 7.03 (t, J=8.8 Hz, 1H), 7.34-7.38 (m, 1H), 7.39 (dd, J=12.1, 2.1 Hz, 1H), 7.56-7.59 (m, 2H), 7.79 (s, 1H), 8.56 (s, 1H), 8.74 (d, J=1.3 Hz, 1H).
$^{13}$C NMR (75 MHz, MeOD) δ 115.9 (d, J=19.2 Hz, 1C), 117.2, 119.4 (d, J=3.3 Hz, 1C), 124.7 (d, J=2.7 Hz, 1C), 126.2 (d, J=6.0 Hz, 1C), 126.8, 129.0, 129.7, 133.3, 135.2, 142.1, 145.5 (d, J=12.6 Hz, 1C), 151.6 (d, J=241.0 Hz, 1C), 153.5, 153.8, 154.1, 159.2.
HRMS (ES+) m/z calculated for $C_{19}H_{14}FN_2O_2$ [M+H]$^+$, 321.1039. found, 321.1045.
IR (cm$^{-1}$) ν 3173, 2922, 1259.
UPLC $R_t$=2.68 min; area 95%.

Example 2

Validation of the Method of In Vitro Measurement and Evaluation of DYRK1A Protein Affinity of the Compounds According to the Invention The validity of the measurement test was first shown by means of measurement of DYRK1A enzyme activity.

The test developed is based on the use of a peptide substrate of DYRK1A having one of its amino acids labeled with fluorescein. The sequence of this peptide (fluorescein-KKISGRLSPIMTEQ) is derived from the Forkhead protein and has a serine residue that can be phosphorylated by DYRK1A. In our test, the peptide phosphorylated by His-DYRK1A-ΔC is separated from the unphosphorylated peptide on a hydrophobic $C_8$ or $C_{18}$ column coupled to an ultra-fast liquid chromatography (UFLC) apparatus with a fluorescence detector. Detection is specific and very sensitive due to the presence in the peptide of the fluorescein group and to the use of a fluorescence detector. Enzymological analyses show that the test is linear as a function of time and of the amount of His-DYRK1A-ΔC enzyme (FIG. 1).

We also determined the IC$_{50}$ values for known DYRK1A inhibitors such as harmine and epigallocatechin-3-gallate (EGCG). Values similar to those of the literature obtained with kinase activity tests using radioactive compounds were obtained.

The IC$_{50}$ values for DYRK1A protein of the various compounds of example 1 were then evaluated. The DYRK1A activity assay is carried out on a 96-well plate in a final volume of 50 μl containing 50 mM TrisHCl pH 7.4, 100 μM EGTA, 1 mM DTT, 5 mM magnesium acetate, 50 to 1000 μM ATP, 5 to 30 μM peptide substrate, and 10 ng of ΔDYRK1A enzyme.

Incubation is carried out at 37° C. and the reaction is quenched at various times by the addition of 50 μl of 15% perchloric acid solution. The plate is then centrifuged and 20 μl of the supernatant is injected into the ultra-fast liquid chromatography system.

The results of these tests are presented in table 1.

TABLE 1

| Example | X$_1$ | X$_2$ | X$_3$ | X$_4$ | X$_5$ | Y$_1$ | Y$_2$ | Y$_3$ | Y$_4$ | Y$_5$ | IC$_{50}$[1] |
|---|---|---|---|---|---|---|---|---|---|---|---|
| A | OH | H | H | H | H | H | H | H | H | H | 3592 |
| B | H | H | H | H | H | H | H | H | H | H | 7490 |
| C | H | H | OH | H | H | H | H | H | H | H | 326 |
| E | H | OH | OH | H | H | H | H | H | H | H | 160 |
| F | OH | H | OH | H | H | H | H | H | H | H | 154 |
| Ia | H | OH | H | H | H | H | OH | H | H | H | 105 |
| Ib | H | H | OH | H | H | H | H | OH | H | H | 23.1 |
| Ic | H | H | OH | H | H | H | F | OMe | H | H | 41.5 |
| I'a | OH | H | OH | H | H | H | H | OH | H | H | 11.7 |
| I'b | H | OH | OH | H | H | H | H | OH | H | H | 3.0 |
| I'c | H | OH | OH | H | H | H | OH | OH | H | H | 12.4 |
| I'd | OH | H | OH | H | H | H | OH | OH | H | H | 14.3 |
| I'e | OH | H | H | OH | H | H | OH | OH | H | H | 39.1 |
| I'f | H | OH | OH | H | H | H | H | F | H | H | 20.7 |
| I'g | H | OH | OH | H | H | F | F | H | H | H | 56.6 |
| I'h | H | H | OH | H | H | H | F | OH | H | H | 9.3 |

[1]IC$_{50}$ is expressed in nanomoles (nmol).

The results show that the compounds of formula (I) and formula (I') have excellent affinity for DYRK1A protein.

Example 3

Evaluation of Cytotoxicity of the Compounds According to the Invention

Cytotoxicity of the compounds according to the present invention was evaluated on cells of the KB line at various concentrations. The measurements were carried out according to the method described in Pons et al. (ACS Medicinal Chemistry Letters, 2011, 2, 565-570). The results of these tests are presented in table 2.

TABLE 2

| Ex. | $X_1$ | $X_2$ | $X_3$ | $X_4$ | $X_5$ | $Y_1$ | $Y_2$ | $Y_3$ | $Y_4$ | $Y_5$ | $10^{-5}\,M^1$ | $10^{-6}\,M^1$ |
|---|---|---|---|---|---|---|---|---|---|---|---|---|
| B   | H  | H  | H  | H | H | H | H | H   | H | H | 85 | 15 |
| C   | H  | H  | OH | H | H | H | H | H   | H | H | 94 | 5  |
| E   | H  | OH | OH | H | H | H | H | H   | H | H | 63 | 12 |
| F   | OH | H  | OH | H | H | H | H | H   | H | H | 75 | 9  |
| Ia  | H  | OH | H  | H | H | H | OH| H   | H | H | 77 | 4  |
| Ib  | H  | H  | OH | H | H | H | H | OH  | H | H | 95 | 51 |
| Ic  | H  | H  | OH | H | H | H | F | OMe | H | H | —² | 23 |
| I'a | OH | H  | OH | H | H | H | H | OH  | H | H | 83 | 21 |
| I'c | H  | OH | OH | H | H | H | OH| OH  | H | H | 11 | 2  |
| I'f | H  | OH | OH | H | H | H | H | F   | H | H | —  | 15 |
| I'g | H  | OH | OH | H | H | H | F | F   | H | H | —  | 22 |
| I'h | H  | H  | OH | H | H | H | F | OH  | H | H | —  | 13 |

[1]Expressed as a percentage of inhibition of KB cell growth.
[2]"—" indicates that the value was not determined.

The compounds of formula (I) and formula (I') have low toxicity on KB cells in amounts much greater than the $IC_{50}$ values measured. The cytotoxicity of compounds of formula (I') is significantly reduced.

Example 4

Tests of In Vivo Activity of the Compounds According to the Invention

To test in vivo the efficacy of these inhibitors, the effect of the compounds according to the invention on the phosphorylation state of two DYRK1A downstream targets in signaling pathways was measured: GSKIII beta protein (FIG. 1a) and CAMKII protein (FIG. 1b).

These measurements were carried out in the brain of control animals (WT) and of animals of an animal model of trisomy for DYRK1A gene (TG).

To that end, the compounds were administered by intraperitoneal injection in the amount of 1 mg/kg at t0 then at t16 (hours) and the animals were sacrificed at t17-t18. Brain proteins were then extracted and the amounts of GSKIIIbeta, pGSKIIIbeta, CAMKII and pCAMKII proteins were measured by a slot-blot technique with suitable antibodies.

The results of these tests are presented in FIG. 1: the y-axis represents the ratio of phosphorylated protein to unphosphorylated protein measured on the untreated animals (WT and TG) and on the animals treated with the compounds according to the invention.

RESULTS

For hyperphosphorylated GSKIIIbeta protein in the TG model animals, an excessive correction with compounds C (TG-C) and I'c (TG-I'c) and an effective correction for compounds Ib (TG-Ib) and I'a (TG-I'a) are observed.

For hypophosphorylated CAMKII protein in the TG model animals, compounds C (TG-C) and I'c (TG-I'c) do not produce a sufficient correction whereas compounds Ib (TG-Ib) and I'a (TG-I'a) return the phosphorylation level to the value observed in the control animals.

The compounds of formula (I) and formula (I') thus have significant inhibitory activity on DYRK1A protein ($IC_{50}$<100 nM), very low cytotoxicity and high activity in vivo on animals of an animal model of trisomy 21.

The invention claimed is:

1. A compound of formula (I') or one of the pharmaceutically acceptable salts, solvates and hydrates thereof:

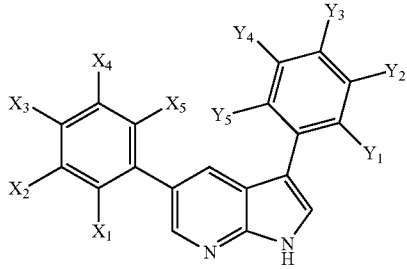

(I')

wherein:
$X_3$ is F, OH or SH,
$Y_3$ is F, OH or SH,
$X_1$, $X_2$, $X_4$, $X_5$, $Y_1$, $Y_2$, $Y_4$ and $Y_5$ independently of one another are H, F, Cl, Br, OH or SH, and
one to two groups among radicals $X_1$, $X_2$, $X_4$ and $X_5$ are different from H and/or one to two groups among radicals $Y_1$, $Y_2$, $Y_4$ and $Y_5$ are different from H.

2. The compound of formula (I') according to claim 1 wherein radicals $X_1$-$X_5$ and $Y_1$-$Y_5$ independently of one another are H, F, OH or SH.

3. The compound of formula (I') according to claim 1 wherein $Y_2$ is different from H.

4. The compound of formula (I') according to claim 1 wherein $X_1$ is different from H.

5. The compound of formula (I') according to claim 1 wherein $X_2$ is different from H.

6. The compound of formula (I') according to claim 1 wherein $X_1$ and $Y_2$ are different from H.

7. The compound of formula (I') according to claim 1 wherein $X_2$ and $Y_2$ are different from H.

8. The compound of formula (I') according to claim 1 wherein at least one radical among $X_1$-$X_5$ and $Y_1$-$Y_5$ is OH.

9. The compound of formula (I') according to claim 1 wherein at least one radical among $X_1$-$X_5$ is OH and at least one radical among $Y_1$-$Y_5$ is OH.

10. A method for the treatment and/or reduction of cognitive disorders associated with dysfunction of DYRK1A protein, with Alzheimer's disease or with Down's syndrome comprising administering a compound of formula (I') according to claim 1 to a patient in need thereof.

11. A pharmaceutical composition comprising at least one compound of formula (I') according to claim 1 and at least one pharmaceutically acceptable excipient.

12. A method for the treatment and/or reduction of cognitive disorders associated with Down's syndrome comprising administering to a patient in need thereof a compound of formula (I):

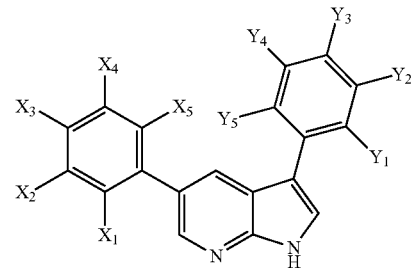

(I)

wherein:
$X_1$-$X_5$ independently of one another are H, F, Cl, Br, $OR_1$ or $SR_2$,
$Y_1$-$Y_5$ independently of one another are H, F, Cl, Br, $OR_3$ or $SR_4$, where
  $R_1$ and $R_3$ independently of one another represent ($C_1$-$C_6$)-alkyl; acyl; optionally substituted aralkyl or optionally substituted aryl,
  $R_2$ and $R_4$ independently of one another represent ($C_1$-$C_6$)-alkyl; acyl; optionally substituted aralkyl or optionally substituted aryl,
one to three radicals among $X_1$-$X_5$ are different from H,
one to three radicals among $Y_1$-$Y_5$ are different from H,
and at least one radical among radicals $X_1$-$X_5$ and $Y_1$-$Y_5$ different from H is F, OH or SH.

13. The method according to claim 12 wherein radicals $X_1$-$X_5$ and $Y_1$-$Y_5$ represent H, F, OH, SH, $OR_1$, $SR_2$, $OR_3$ or $SR_4$.

14. The method according to claim 12 wherein at least one radical among $X_1$-$X_5$ is F, OH or SH, and at least one radical among $Y_1$-$Y_5$ is F, OH or SH.

15. The method according to claim 12 wherein $X_3$ and $Y_3$ are different from H.

16. The method according to claim wherein $X_1$, $Y_2$ and $Y_3$ are different from H.

17. The method according to claim 12 wherein $X_3$, $Y_2$ and $Y_3$ are different from H.

18. The method according to claim 12 wherein $X_2$, $X_3$ and $Y_3$ are different from H.

19. The method according to claim 12 wherein $X_1$, $X_3$, $Y_2$ and $Y_3$ are different from H.

20. The method according to claim 12 wherein $X_2$, $X_3$, $Y_2$ and $Y_3$ are different from H.

21. The method of claim 12 wherein the compound is administered as a pharmaceutical composition.

22. A method for the preparation of a compound of formula (I') according to claim 1 or one of the pharmaceutically acceptable salts, solvates and hydrates thereof comprising the steps of:

(a) reaction between a compound of formula (II'):

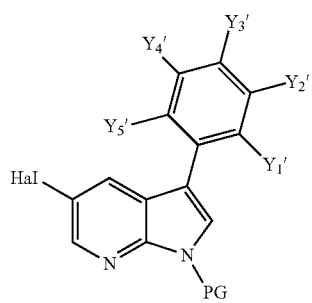

(II')

and a compound of formula (III'):

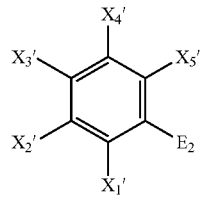

(III')

wherein:
PG represents an N-protecting group,
Hal represents a halogen atom, in particular bromine, or an OSO$_2$CF$_3$ group,
E$_2$ represents a boronic acid B(OH)$_2$ or a derivative thereof,
radicals X$_{3'}$ and Y$_{3'}$ are F, OPG$_1$ or SPG$_2$, where PG$_1$ represents an O-protecting group and PG$_2$ represents an S-protecting group, radicals X$_1$, X$_2$, X$_4$, X$_5$, Y$_1$, Y$_2$, Y$_4$ and Y$_5$ independently of one another are H, F, Cl, Br, OPG$_1$ or SPG$_2$,
PG$_1$ represents an O-protecting group and PG$_2$ represents an S-protecting group, to yield a compound of formula (IV'):

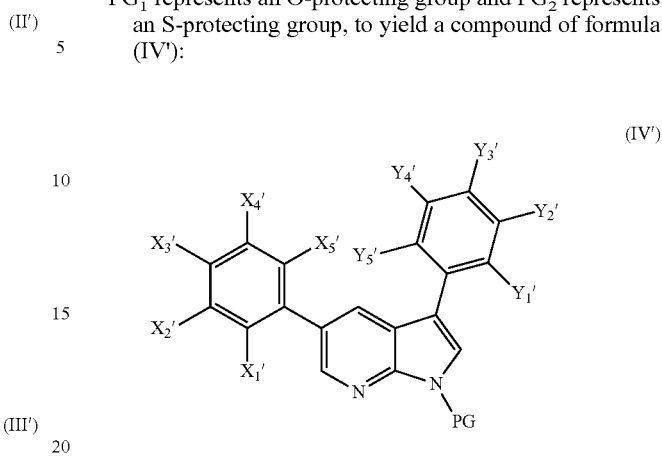

(IV')

(b) deprotection of the N-PG group of the compound of formula (IV') and the OPG$_1$ and SPG$_2$ groups to yield a compound of formula (I'), (c) optionally salification, solvation or hydration to yield a pharmaceutically acceptable salt, solvate or hydrate of a compound of formula (I').

23. A method for inhibiting DYRK1A protein activity in a patient with cognitive disorders associated with dysfunction of DYRK1A protein, with Alzheimer's disease or with Down's syndrome comprising administering a compound of formula (I') according to claim 1 to the patient.

24. A method for inhibiting DYRK1A protein activity in a patient with cognitive disorders associated with Down's syndrome comprising administering a compound of formula (I) according to claim 12 to the patient.

* * * * *